(12) United States Patent
Saigh

(10) Patent No.: US 10,660,546 B2
(45) Date of Patent: May 26, 2020

(54) HUMAN AND ANIMAL PHYSIOLOGICAL COMPARATIVES, COMMUNICATION AND DEVELOPERS' TOOL KIT

(71) Applicant: Michael Saigh, Clayton, MO (US)

(72) Inventor: Michael Saigh, Clayton, MO (US)

(*) Notice: Subject to any disclaimer, the term of this patent is extended or adjusted under 35 U.S.C. 154(b) by 0 days.

(21) Appl. No.: 15/850,291

(22) Filed: Dec. 21, 2017

(65) Prior Publication Data
US 2019/0192053 A1 Jun. 27, 2019

(51) Int. Cl.
| | |
|---|---|
| *A61B 5/11* | (2006.01) |
| *A61B 5/01* | (2006.01) |
| *A61B 5/00* | (2006.01) |
| *A61B 5/0205* | (2006.01) |
| *A61B 5/024* | (2006.01) |
| *A61B 5/145* | (2006.01) |
| *G16H 20/00* | (2018.01) |

(52) U.S. Cl.
CPC ............ *A61B 5/1118* (2013.01); *A61B 5/01* (2013.01); *A61B 5/02055* (2013.01); *A61B 5/11* (2013.01); *A61B 5/1121* (2013.01); *A61B 5/682* (2013.01); *A61B 5/0022* (2013.01); *A61B 5/02438* (2013.01); *A61B 5/14532* (2013.01); *A61B 5/14542* (2013.01); *A61B 5/6814* (2013.01); *A61B 5/6824* (2013.01); *A61B 2503/10* (2013.01); *A61B 2503/40* (2013.01); *A61B 2562/0219* (2013.01); *A61B 2562/0285* (2013.01); *A63B 2225/50* (2013.01); *G16H 20/00* (2018.01)

(58) Field of Classification Search
CPC .................................................. A61B 5/1118
USPC ........................................................ 340/573.1
See application file for complete search history.

(56) References Cited

U.S. PATENT DOCUMENTS

| | | | | |
|---|---|---|---|---|
| 9,872,481 | B2* | 1/2018 | Goldfain | A01K 29/005 |
| 2014/0378853 | A1* | 12/2014 | McKinney | A61B 5/02438 |
| | | | | 600/509 |
| 2015/0185088 | A1* | 7/2015 | Rabieirad | A61B 5/01 |
| | | | | 374/122 |
| 2016/0100758 | A1* | 4/2016 | Jeong | G06F 1/1684 |
| | | | | 340/870.07 |
| 2016/0135431 | A1* | 5/2016 | Sheldon | H02J 7/0047 |
| | | | | 119/859 |
| 2016/0165852 | A1* | 6/2016 | Goldfain | A01K 29/005 |
| | | | | 340/573.3 |
| 2016/0165853 | A1* | 6/2016 | Goldfain | A01K 29/005 |
| | | | | 340/573.3 |

(Continued)

*Primary Examiner* — Santiago Garcia
(74) *Attorney, Agent, or Firm* — Polsinelli PC; Elton F. Dean, III

(57) ABSTRACT

A sports training and guidance platform network which intertwine various wearables is provided. The network includes at least one wearable containing one biosensor worn on a human body and one worn on a animal body, Timestamp biometric and other measurements and inputs from a data stream for both human and animals collected, analyzed, compared and accessed on one or more mobile device platforms. According, the wearable network will measure and compare various animal biosensor data, and motion i.e., accelerometers, gyroscopes with human biosensor data. A sports training toolkit which includes wearable biosensors, sensors, secure wearable communication network(s) and platform and system, applications and database information is also provided.

20 Claims, 25 Drawing Sheets

(56) References Cited

U.S. PATENT DOCUMENTS

| | | | |
|---|---|---|---|
| 2016/0173440 A1* | 6/2016 | Stahura | H04L 61/1511 |
| | | | 709/245 |
| 2016/0174099 A1* | 6/2016 | Goldfain | G16H 40/63 |
| | | | 375/130 |
| 2016/0178392 A1* | 6/2016 | Goldfain | G16H 40/63 |
| | | | 702/104 |
| 2016/0344740 A1* | 11/2016 | Choi | H04L 63/102 |
| 2017/0091412 A1* | 3/2017 | Johnson | G06F 19/36 |
| 2017/0108236 A1* | 4/2017 | Guan | F24F 11/0012 |
| 2017/0135315 A1* | 5/2017 | Marmen | A01K 15/021 |
| 2017/0180959 A1* | 6/2017 | Kim | G16H 10/60 |
| 2017/0334354 A1* | 11/2017 | Hatton | G08G 1/00 |
| 2018/0014512 A1* | 1/2018 | Arabani | A01K 29/005 |
| 2018/0040231 A1* | 2/2018 | DeLuca | A61B 5/02438 |
| 2018/0064068 A1* | 3/2018 | McKee | A01K 27/009 |
| 2019/0059325 A1* | 2/2019 | DeLuccia | A01K 15/021 |
| 2019/0133500 A1* | 5/2019 | Basu | A61B 5/1477 |

* cited by examiner

FIG. 2. Configuration of Storage Database

FIG. 3. Registration and Packages

FIG. 4. Player Profile, Analytics and Report

FIG. 5. Wearable Sports Communication Network

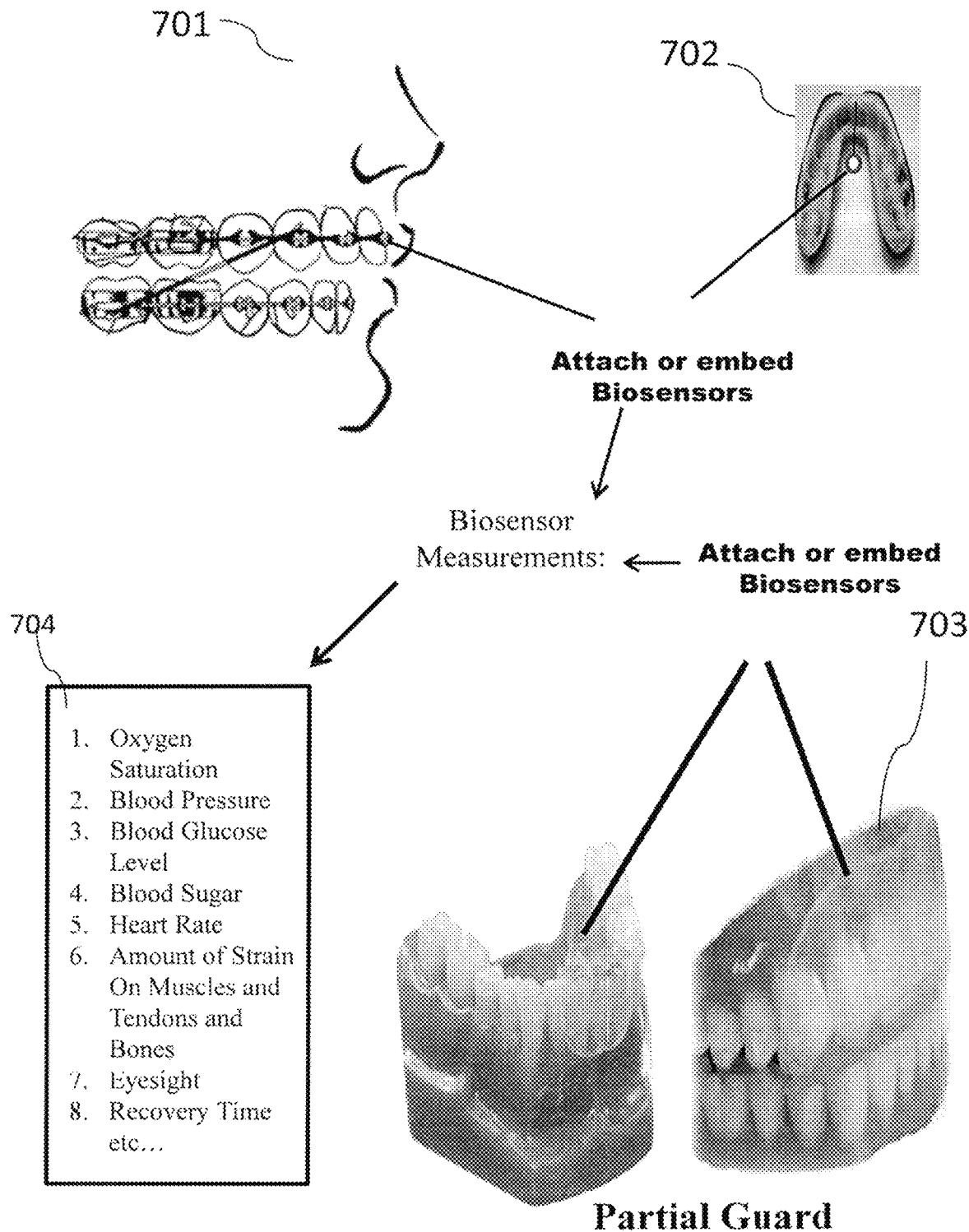
FIG. 7. Smart Sport Guards

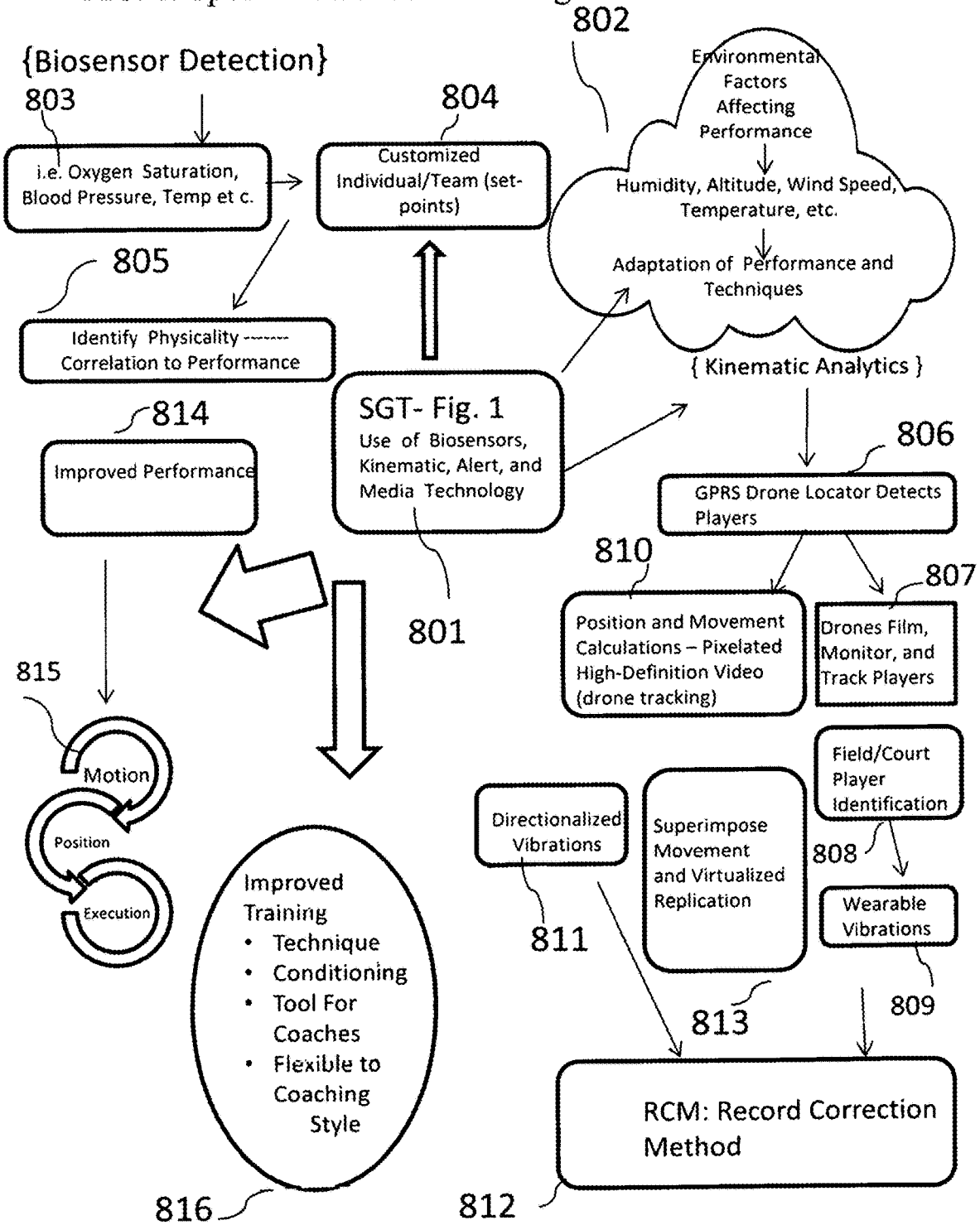
FIG. 8. Sports Guidance Technologies

FIG. 9. Environmental Factors – External Integration

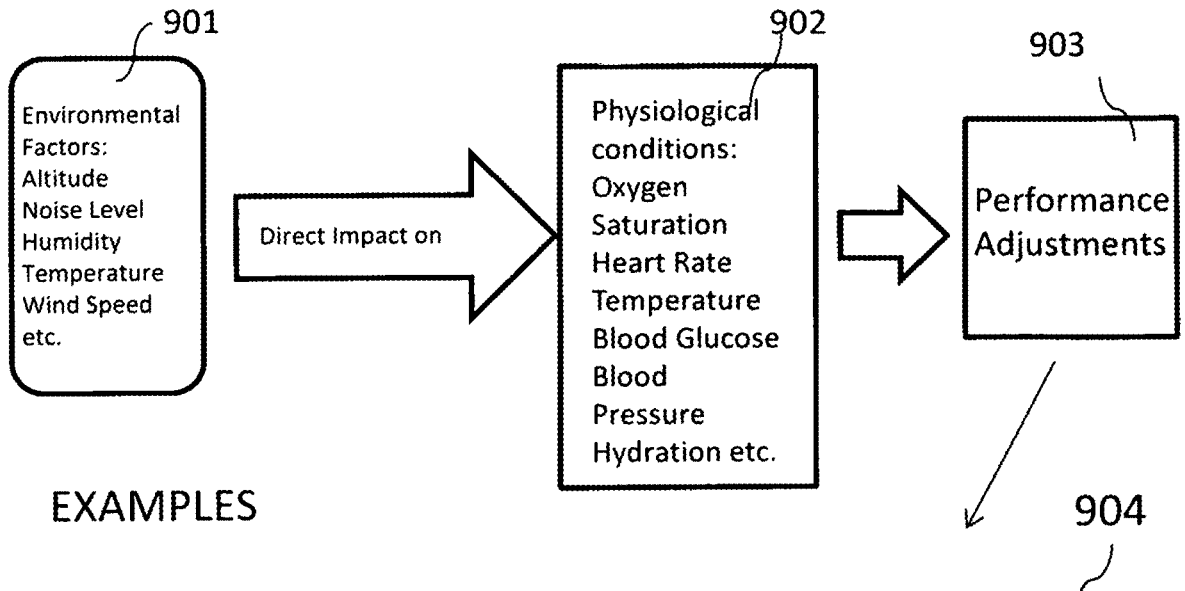

EXAMPLES

| Sensor Detection: Environmental | Device Evaluation: Physiological Effect | Adjustment |
|---|---|---|
| High Altitude | Lowered Oxygen Levels Affects Muscle Activity | • Conservative play<br>• Using More Muscles |
| High Noise Level | Psychological Stimulation | • Breathing Techniques to Calm the Body |
| High Temperature | Increased Rate of Fatigue | • Increased Substitution Rate |
| Wind Speed | Lowered Accuracy In Football Throws | • Throwing Adjustment Based on Kinematic Analysis |
| Low Temperature | Lowered Muscle Activity | • Emphasis on Warm ups |
| Rain-wet ground- Football | Increased Chance Of Improper Footing | • Staggered Steps<br>• Emphasis On Passing |
| Low Humidity | Lowered Hydration Levels | • Drink Water |

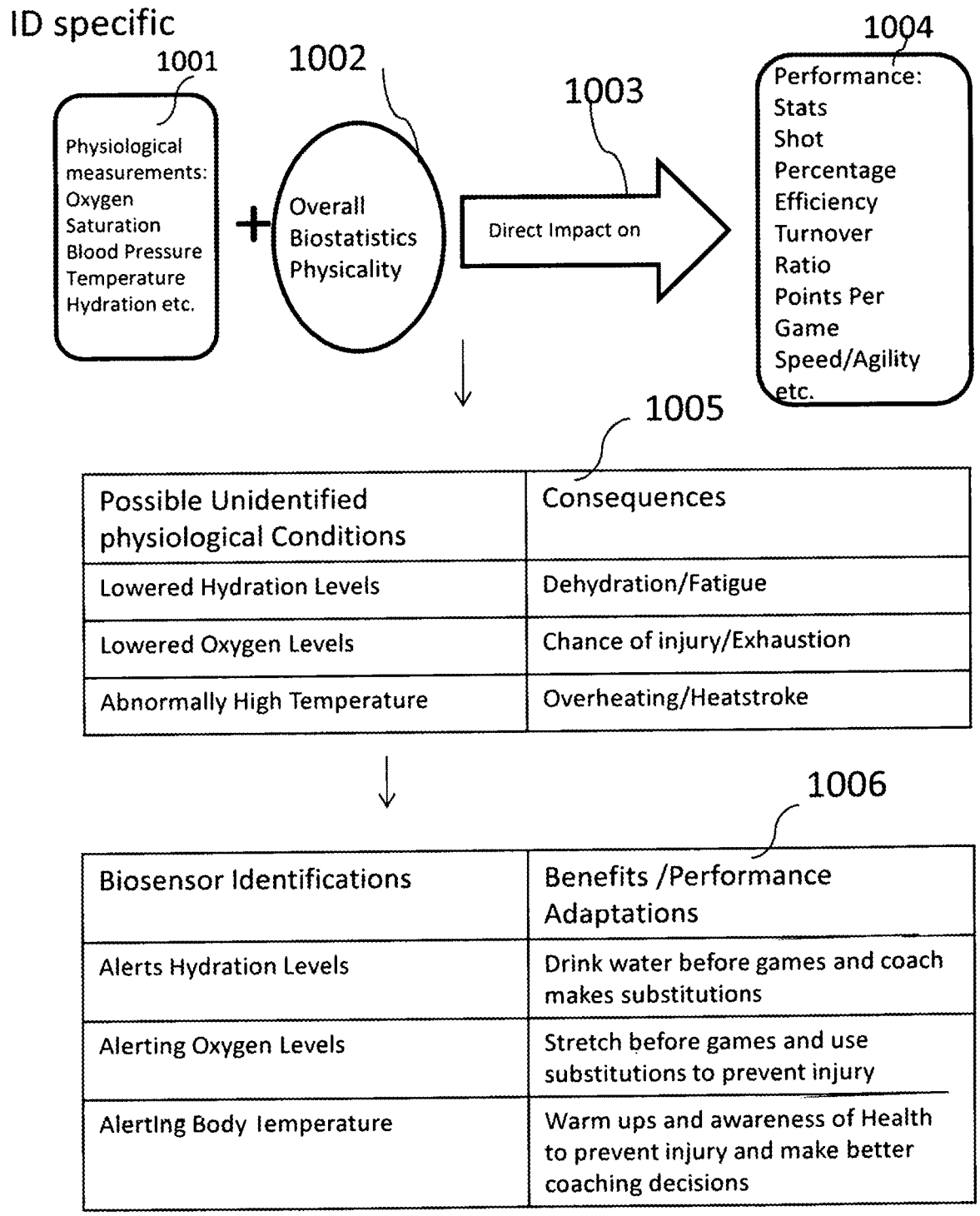
FIG. 10. Physiological measurements in Relation to Performance

FIG. 11. Sensor Set Points, Data Report and Alert

1101

| Physiological Parameters | Extreme Low | Intermediate Low | Safe Low | Safe High | Intermediate High | Extreme High |
|---|---|---|---|---|---|---|
| Temperature(°C) | 28 | 35 | 36.1 | 37.2 | 38 | 40 |
| Oxygen Saturation (%) | 80 | 90 | 95 | 100 | | |
| Heart Rate (bpm) | | <60 | 60 | 100 | >100 | |
| Blood Sugar (fasting) (mg/dL) | 40 | | 70 | 80 | 100 | 126 |

Biosensors Track Physiological characteristics of Each Player on the Team Throughout a Period of Physical Activity, i.e. Oxygen Saturation Levels →

| Time (min) | John | Tom | Tim | Jake | Bart | Jim | Team |
|---|---|---|---|---|---|---|---|
| 0 | 97 | 97 | 98 | 98 | 97 | 99 | 97.8 |
| 1 | 96 | 96.4 | 97.4 | 97.4 | 97.1 | 99 | 97.5 |
| 2 | 96.3 | 96 | 97 | 97 | 96.7 | 99 | 97.1 |
| 3 | 96 | 95.4 | 96.4 | 96.3 | 96 | 99 | 96.6 |
| 4 | 95.5 | 94.6 | 95.6 | 96.1 | 95.8 | 99 | 96.2 |
| 5 | 95.3 | 93.8 | 94.8 | 95.8 | 95.5 | 99 | 95.8 |
| 6 | 95 | 93.2 | 94.2 | 95.6 | 95.3 | 99 | 95.5 |
| 7 | 94.3 | 92 | 93.3 | 95.5 | 95.2 | 98.6 | 94.9 |
| 8 | 93.8 | 93.5 | 93.1 | 95.4 | 95.1 | 99 | 95.2 |
| 9 | 93.5 | 94.5 | 92.8 | 95.3 | 95 | 99 | 95.3 |
| 10 | 93.3 | 95.5 | 92.6 | 95.2 | 94.9 | 99 | 95.4 |
| 11 | 92.5 | 96.5 | 92.4 | 95.1 | 94.8 | 99 | 95.6 |
| 12 | 91.8 | 96.7 | 92.2 | 95 | 94.7 | 99 | 95.5 |
| 13 | 91.5 | 96.9 | 93.5 | 94.8 | 94.5 | 98.4 | 95.6 |
| 14 | 91.2 | 97 | 94.5 | 94.6 | 94.3 | 98 | 95.7 |
| 15 | 90.8 | 97 | 95.5 | 94.4 | 94.1 | 97.5 | 95.7 |
| 16 | 90.5 | 97 | 96.5 | 94.2 | 93.9 | 97 | 95.7 |
| 17 | ((( 90 ))) | 97 | 97.1 | 93.9 | 93.6 | 96.7 | 95.7 |
| 18 | 93 | 96.4 | 97.3 | 93.8 | 93.5 | 96.4 | 95.5 |
| 19 | 96 | 96.2 | 97.3 | 93.8 | 93.5 | 96.3 | 95.4 |
| 20 | 96 | 96.2 | 97.3 | 93.8 | 93.5 | 96.3 | 95.4 |

1102

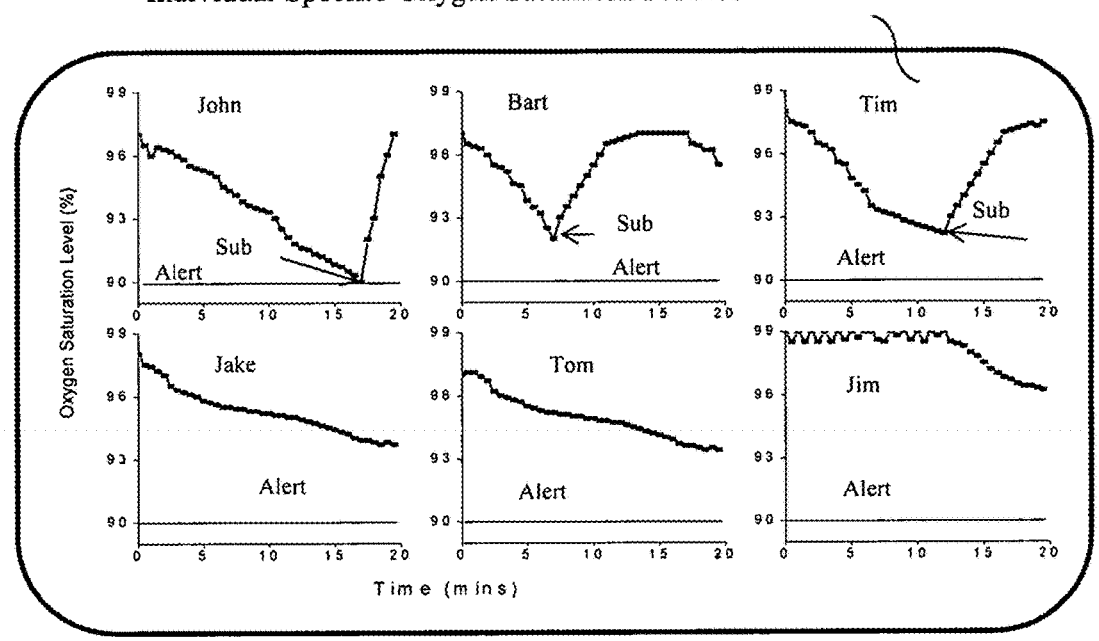
FIG. 12. Graphical Representation of Data Report and Alert

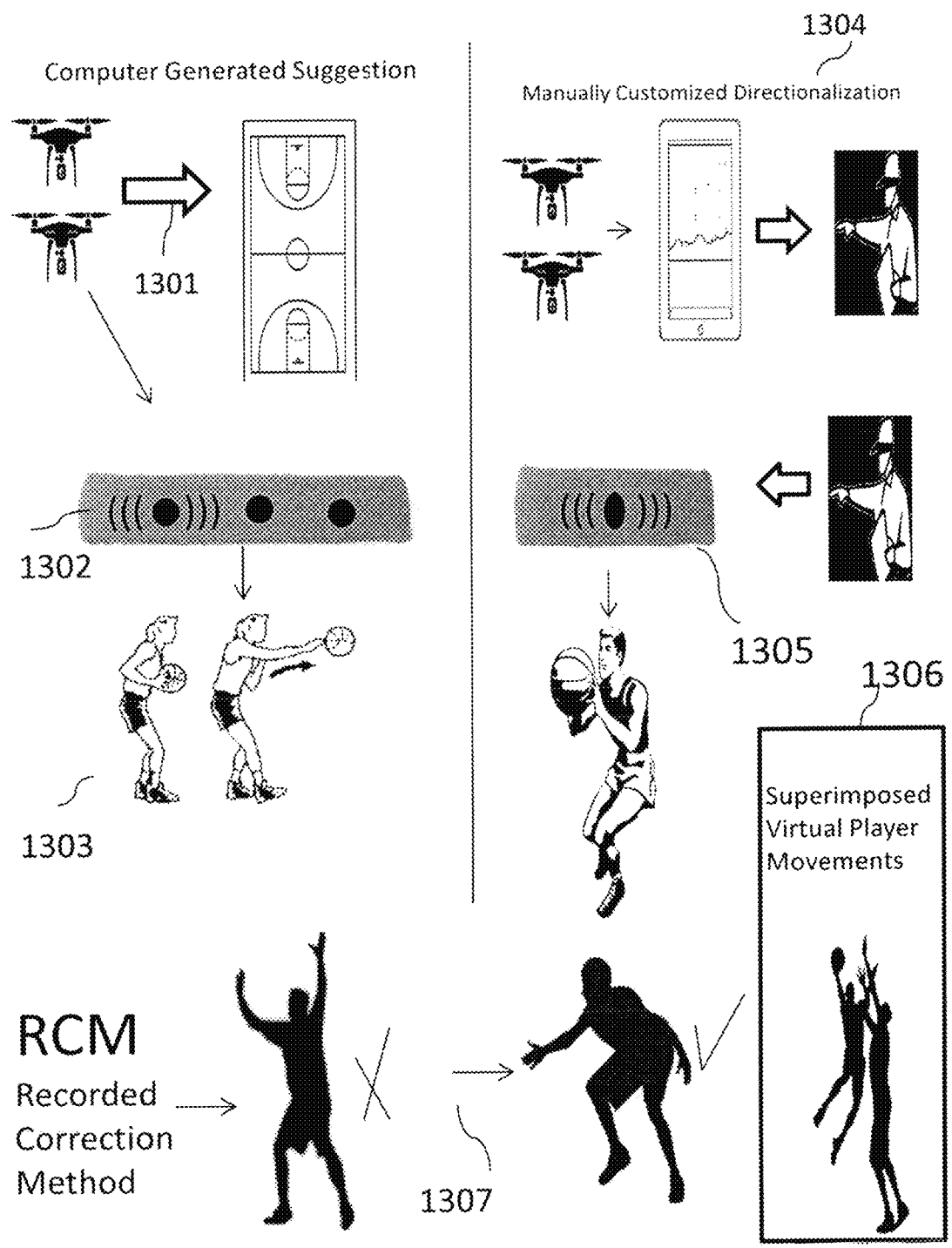
FIG. 13. Direction Guidance

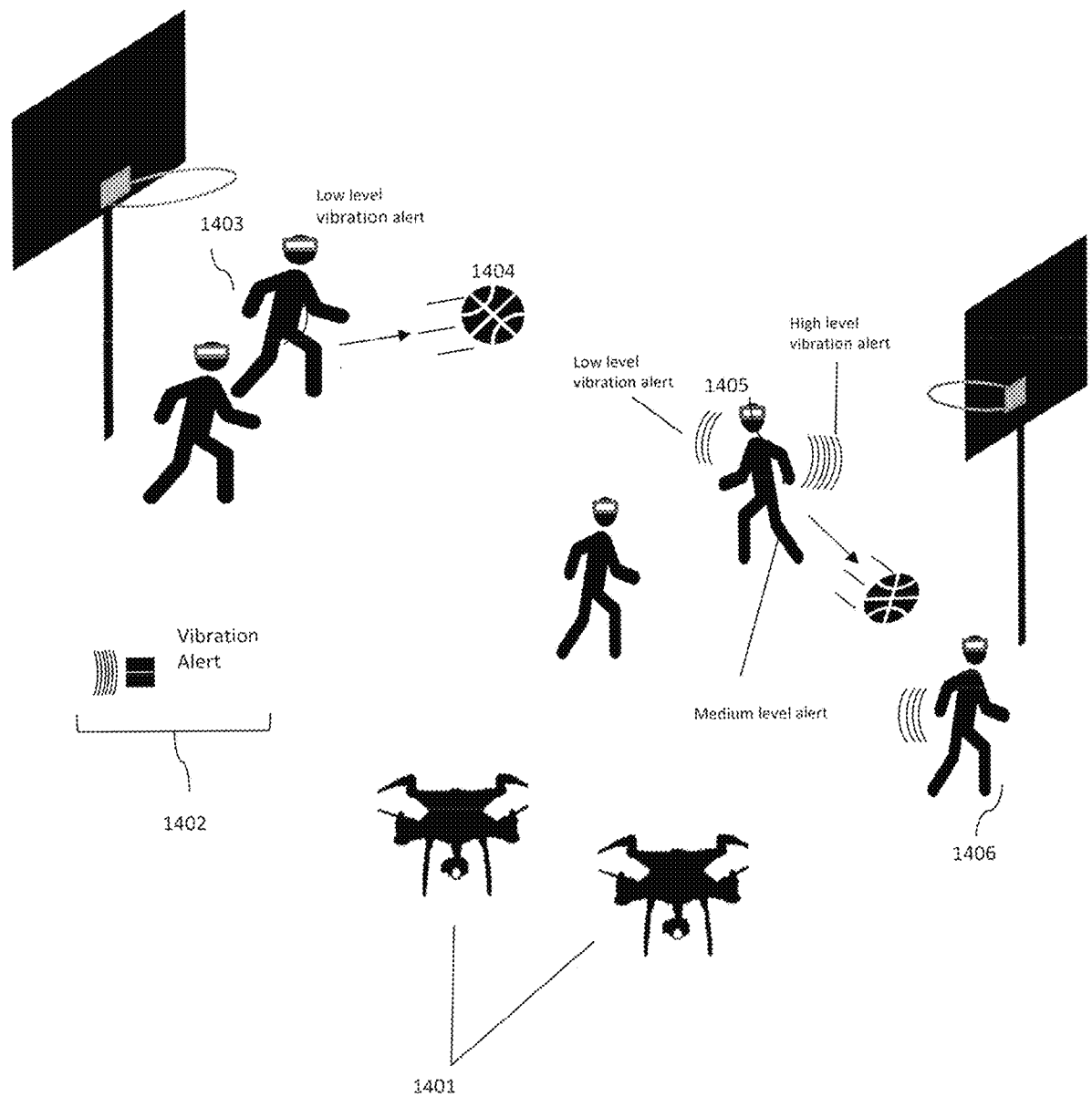
FIG. 14. SGT Device Kinematic Guidance

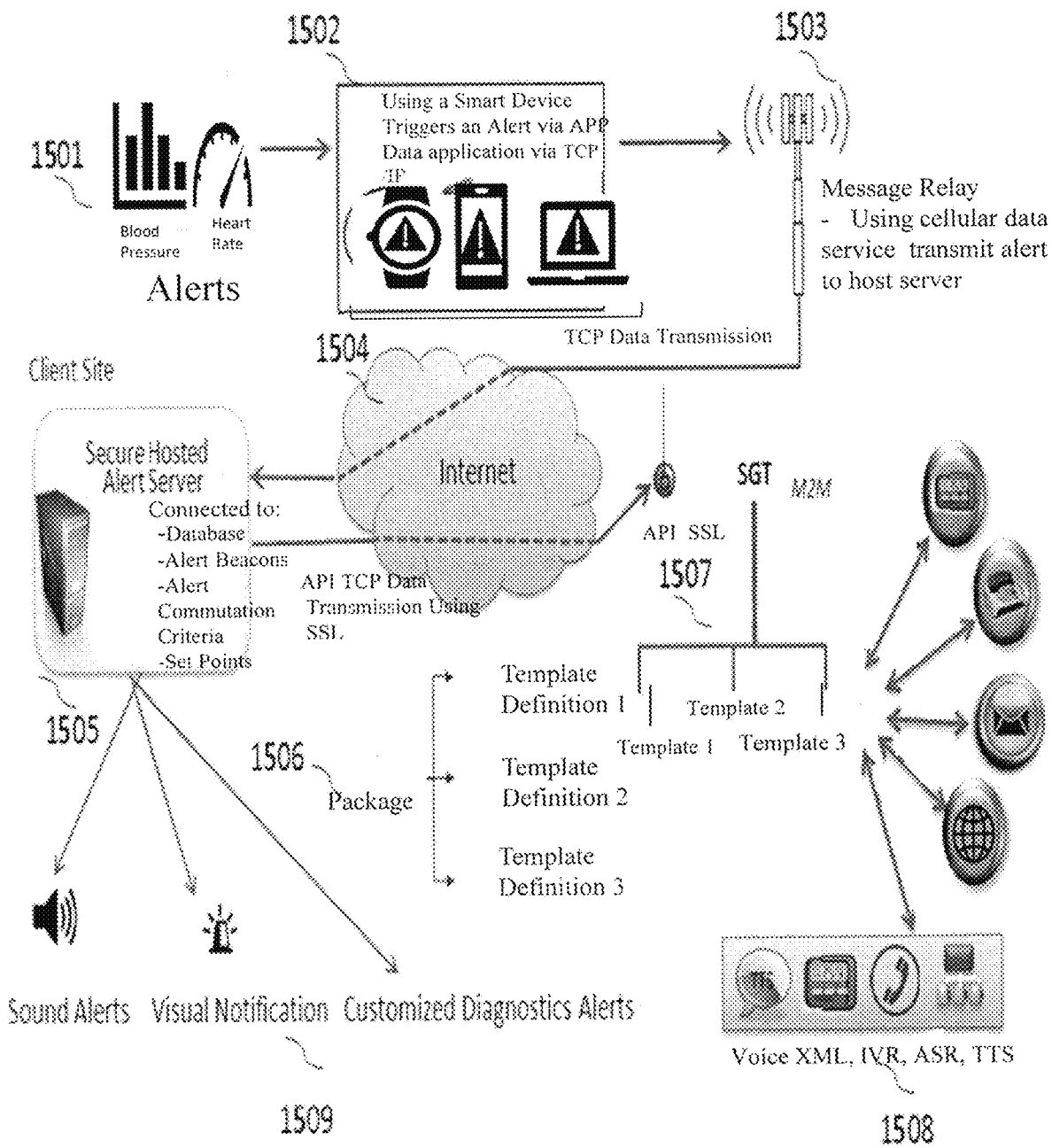
FIG. 15. Wearable Sports Alerting Architecture

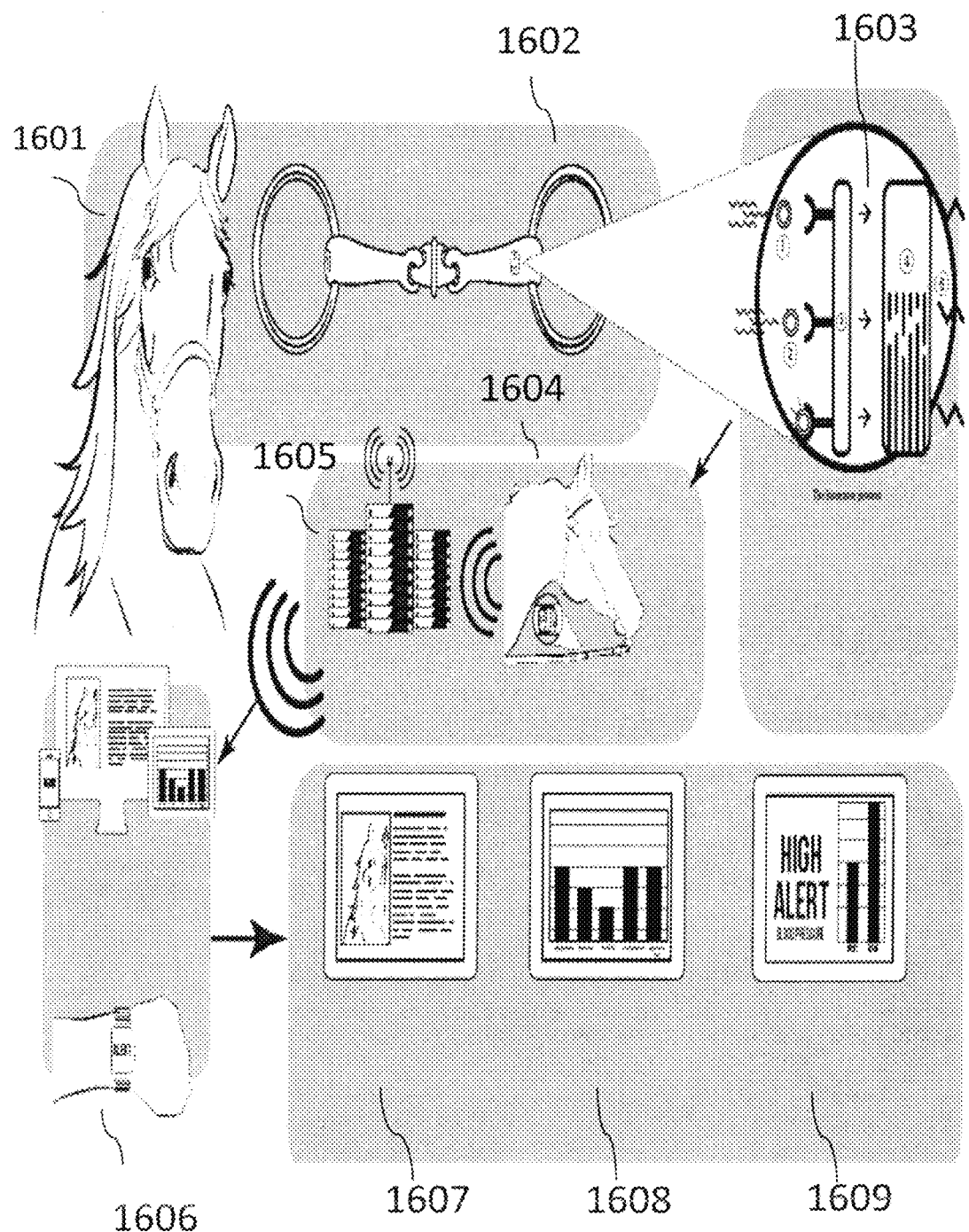
FIG. 16. A Wearable Sports System for Racing Horses

FIG. 17. Examples of Wearable Network Integration
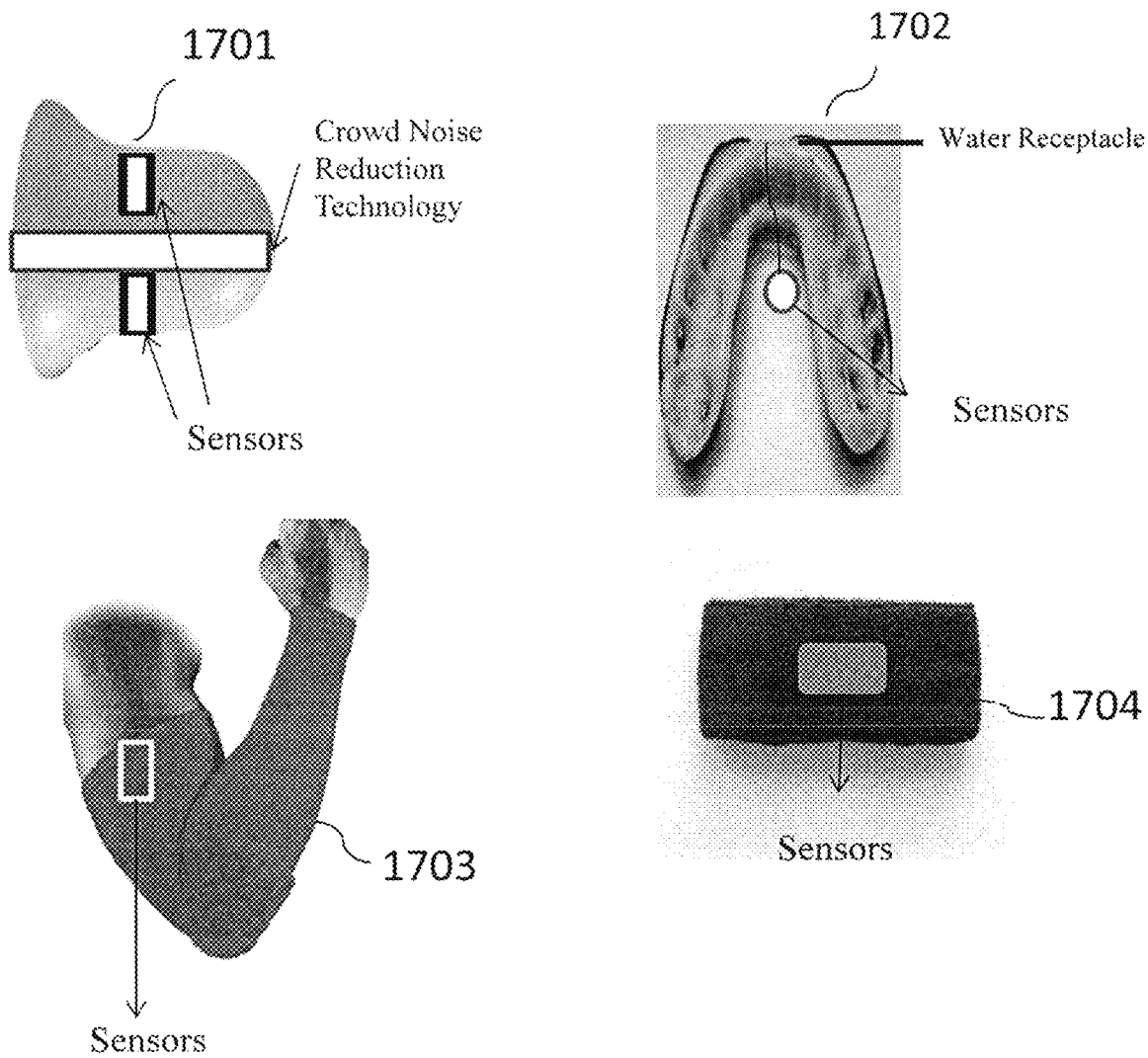

FIG. 18.(a) Examples of Wired Wearable Hardware
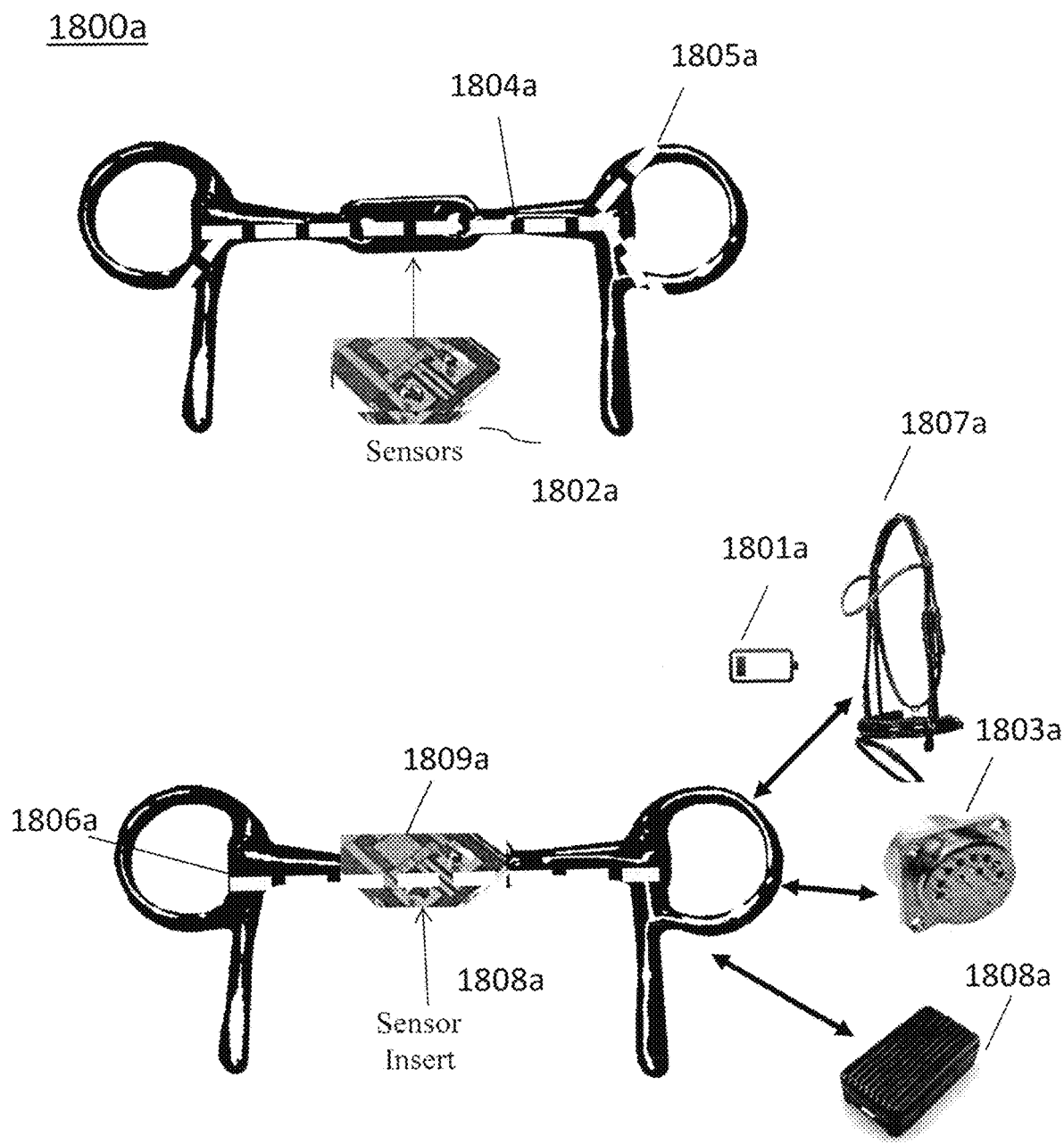

FIG. 18(b). Examples of Wireless wearable Hardware
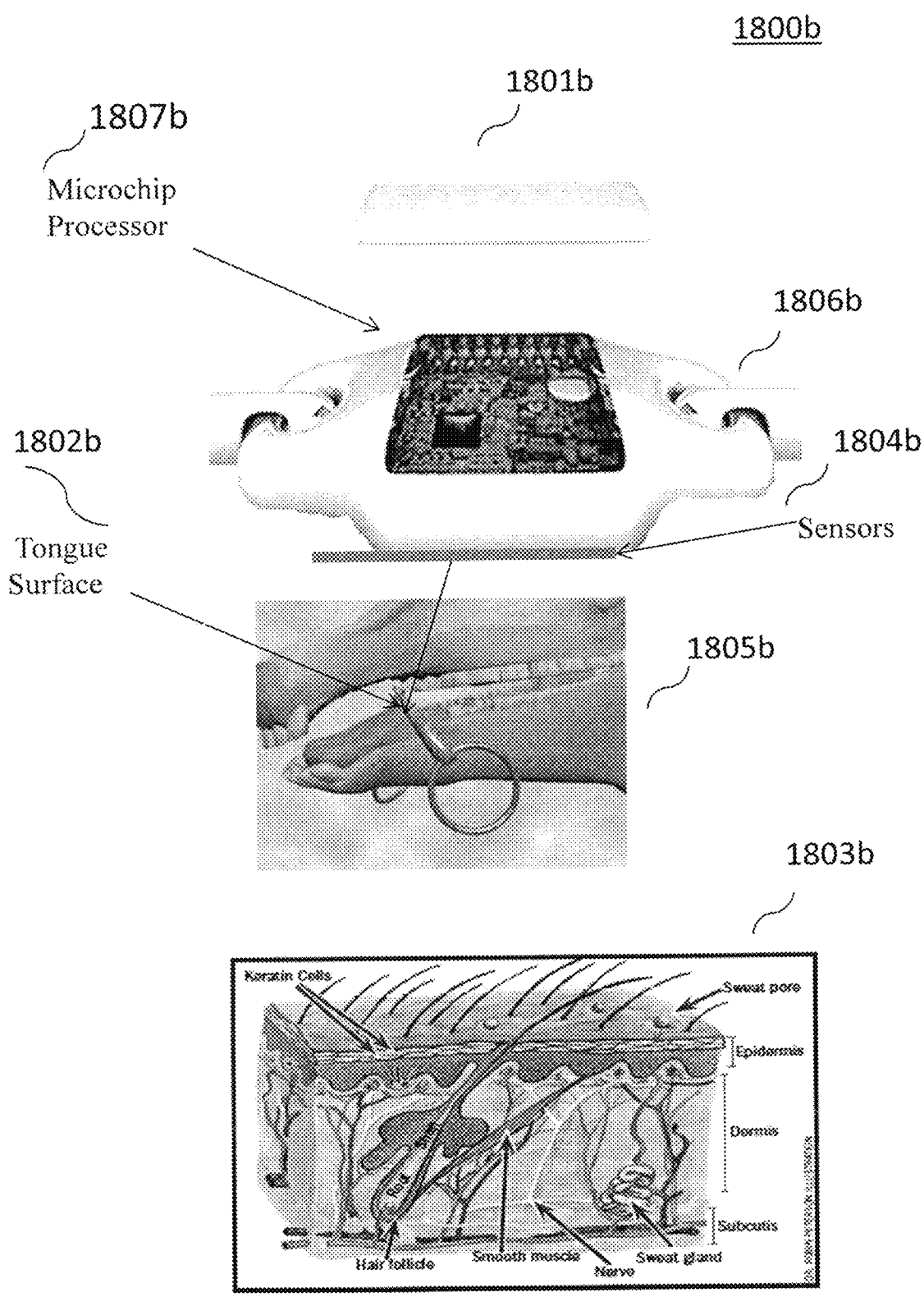

FIG. 19. Animal/ Human(s) Communication Integration
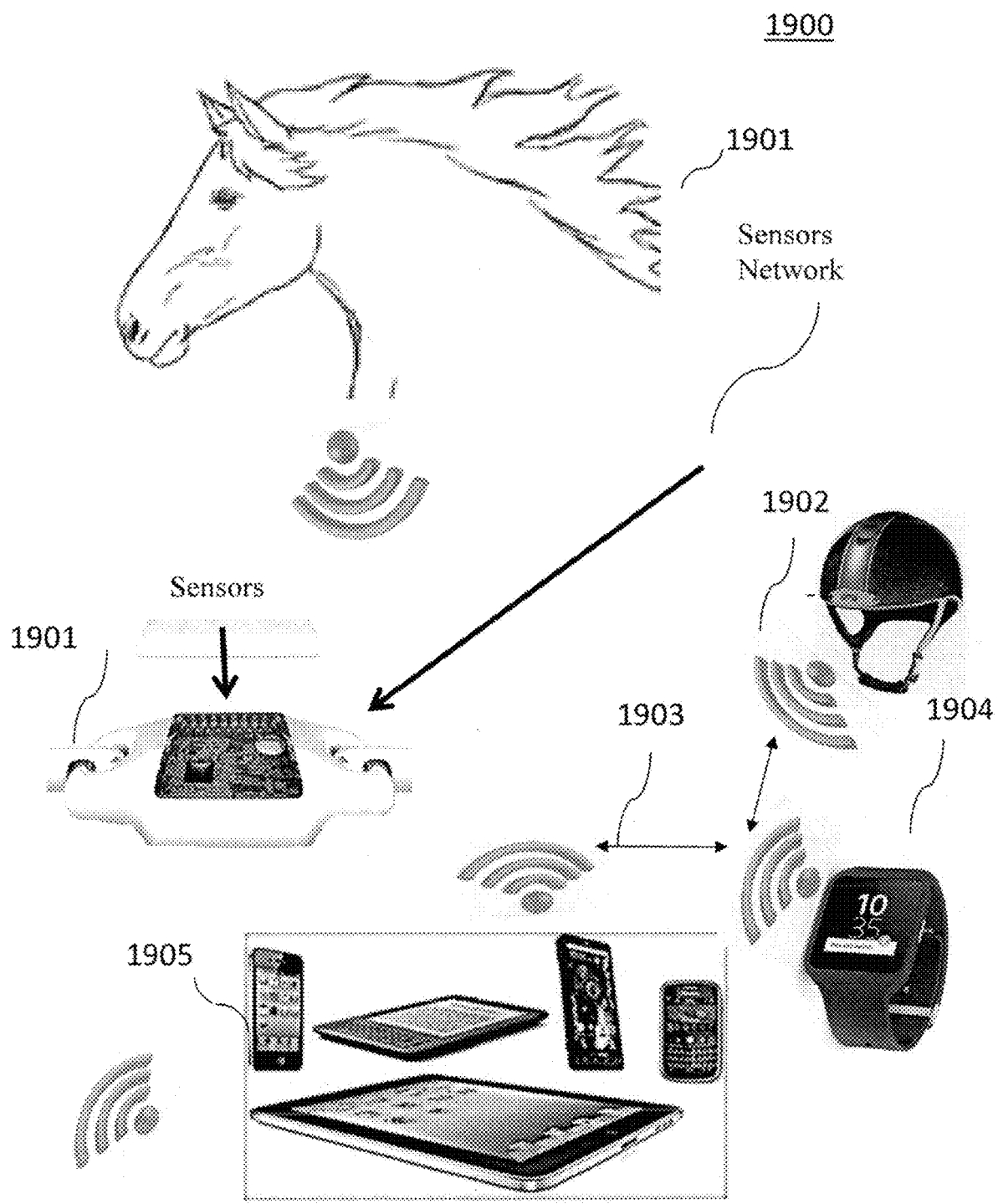

FIG. 20. Mobile Software Analytics
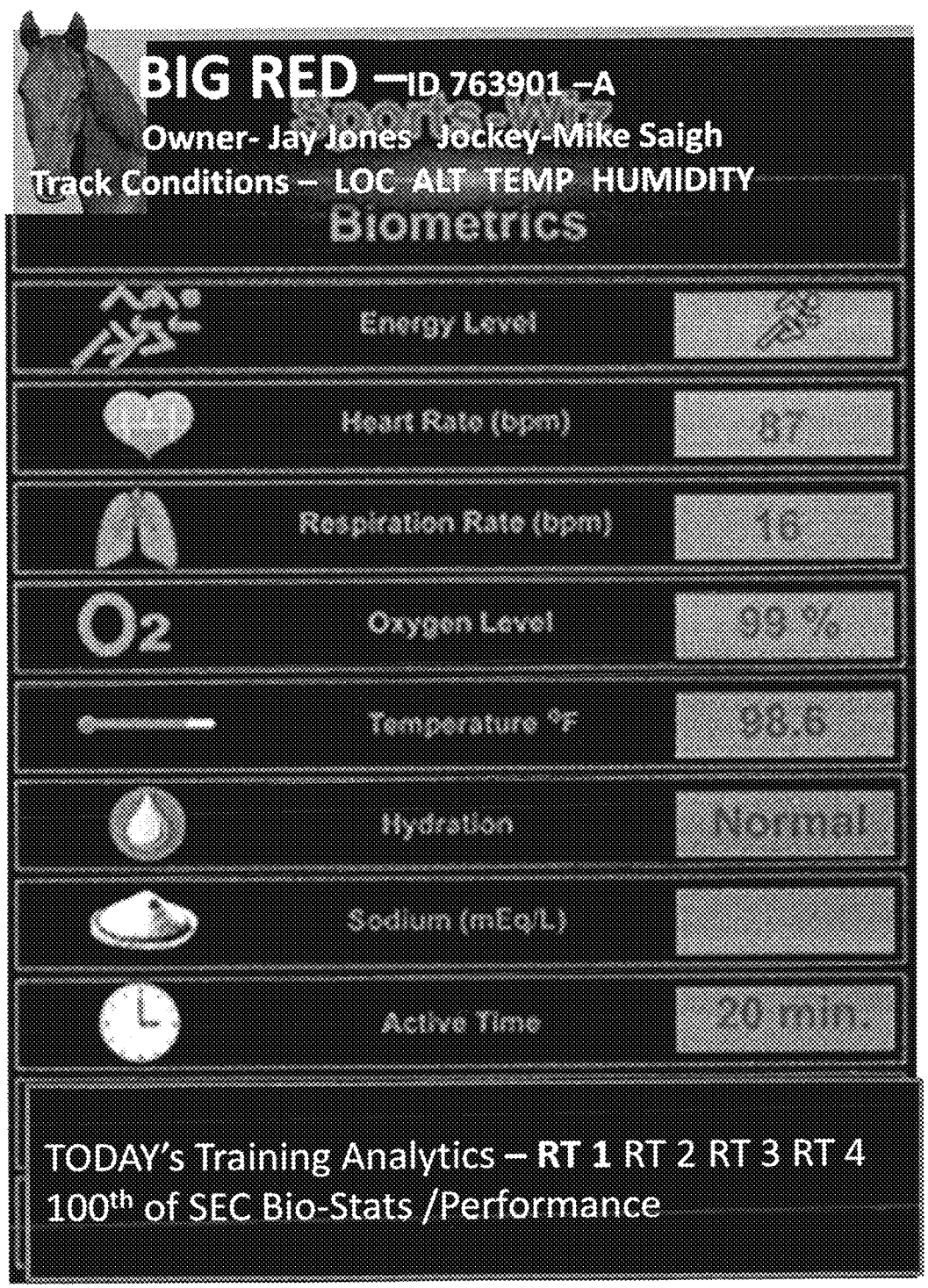

FIG. 21. Examples of physiological analytics vs. Performance Alerting time
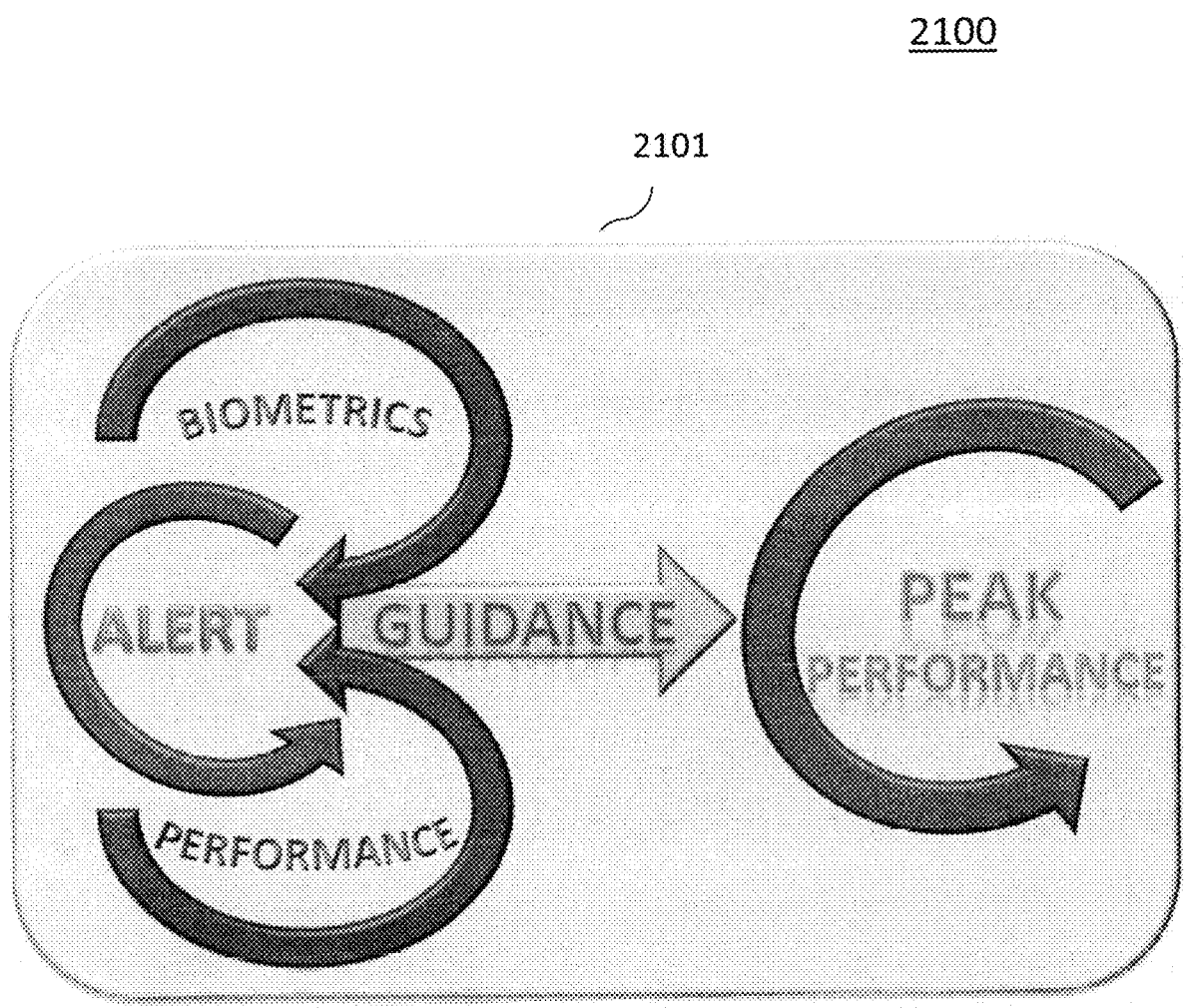

FIG. 22 Equine Gait, Speed Distance, etc.
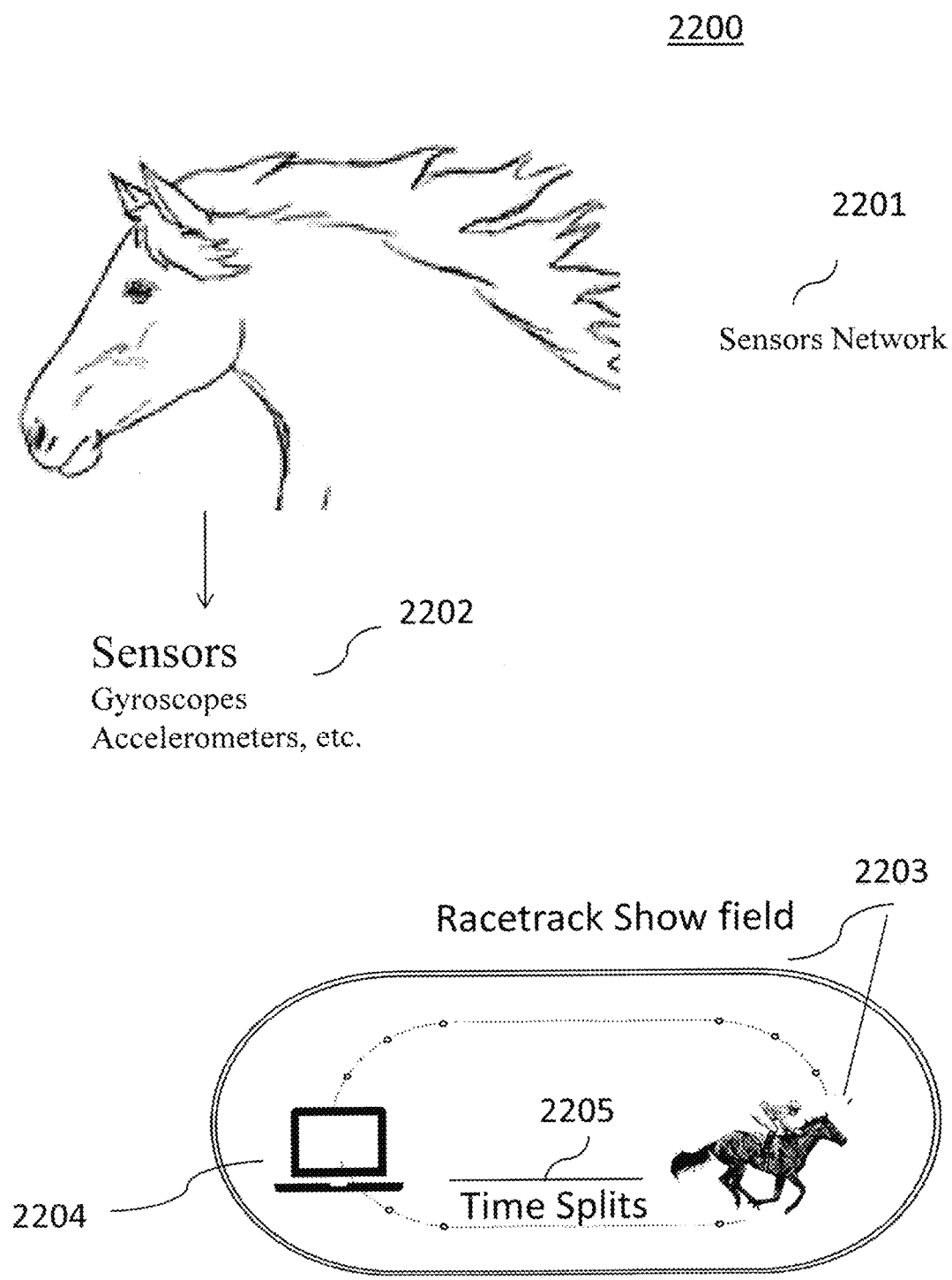

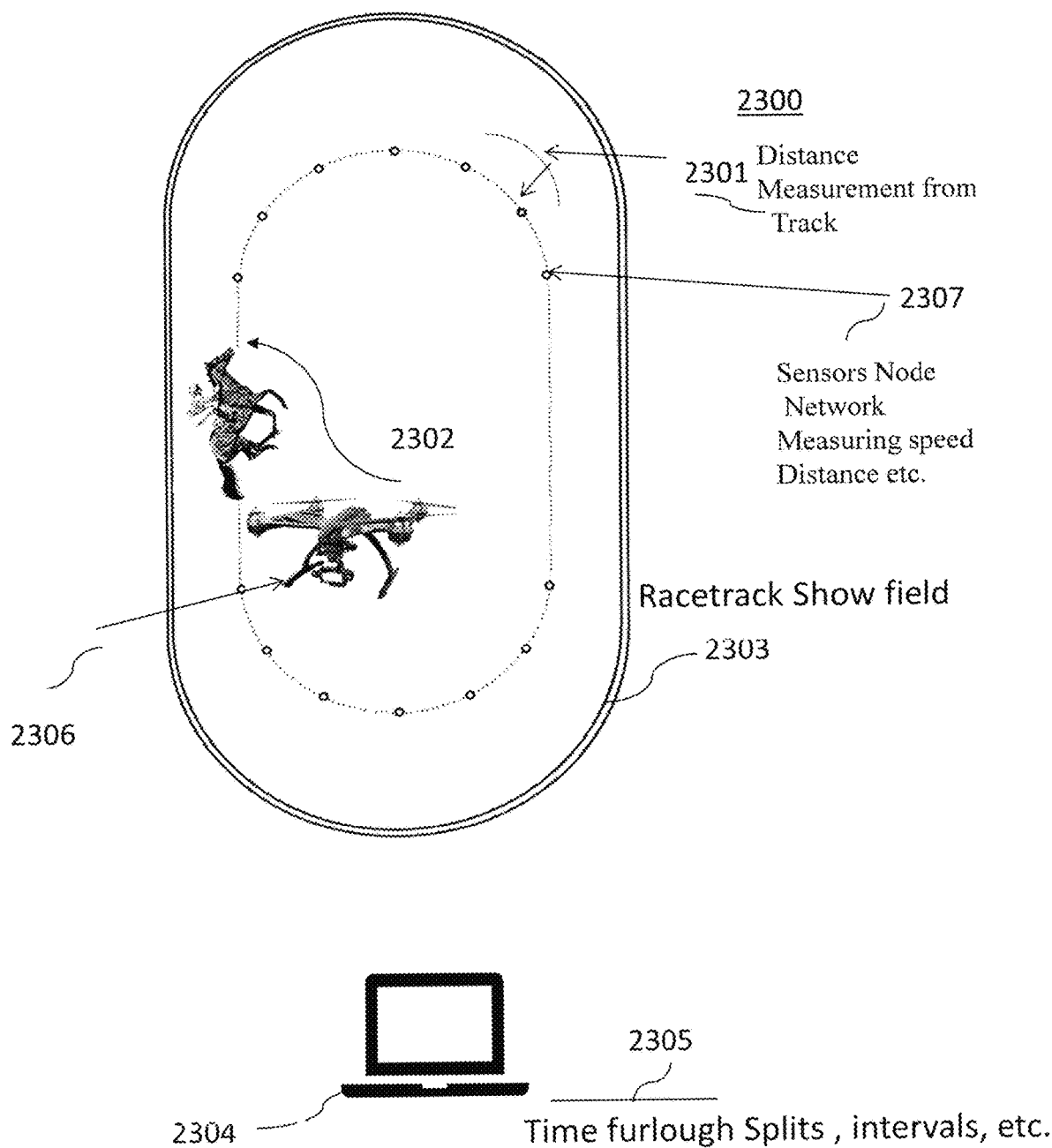
FIG. 23 Equine Gate and Speed.

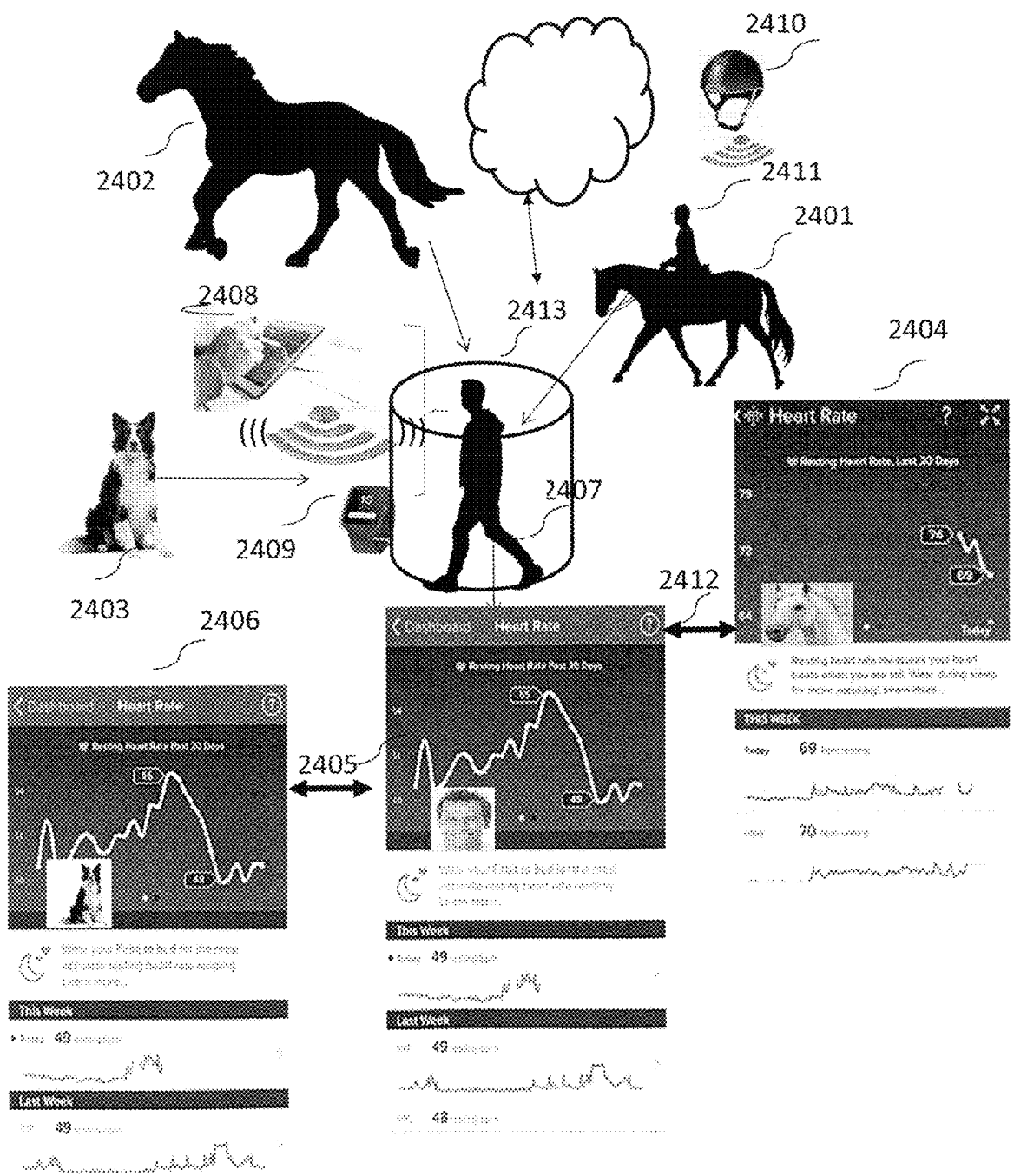
FIG. 24 Example of Human and Animal Physiological Data Measurement Comparatives and Communication

HUMAN AND ANIMAL PHYSIOLOGICAL COMPARATIVES, COMMUNICATION AND DEVELOPERS' TOOL KIT

CROSS-REFERENCE TO RELATED APPLICATIONS

This application claims priority to U.S. provisional application No. 62/440,072, filed on Dec. 29, 2016, which is incorporated herein by reference as though fully set forth herein.

This US provisional application and continuation in part, and claims the benefits of the filing date of U.S. Patent App. No. 62/180,841 entitled "Oral Biosensor Alerts and Communication System" which was filed on Jun. 17, 2015; U.S. patent application Ser. No. 14/850,713 entitled "Oral Sensor Alerting and Communication System and Developers' Tool Kit" which was filed on Sep. 10, 2015; U.S. Pat. App. No. 62/285,454 entitled "Oral Sensor Alerting and Communication System and Developers' Tool Kit" which was filed on Oct. 30, 2015; U.S. Pat. App. No. 62/285,605 entitled "Time Stamped Medication Analytics and Diagnostic System" which was filed on Nov. 2, 2015; U.S. Pat. App. No. 62/295,949 entitled "Network of Wearable Communication System for Biometric and Diagnostic Measurements" which was filed on Feb. 16, 2016; U.S. Pat. App. No. 62/295,959 entitled "Network of Wearable Communication System for Drug Delivery" which was filed on Feb. 16, 2016. These previous patents are incorporated herein by reference. This application is a provisional application filed date on Jun. 23, 2016 and the teachings of which are incorporated herein in their entireties by reference.

STATEMENT REGARDING FEDERALLY SPONSORED RESEARCH OR DEVELOPMENT

The present disclosure relates generally to smart, oral and other sensor technologies and devices and the integration of such with mobile communications, related technologies between both animals and humans, referred to herein as a HUMAN AND ANIMAL PHYSIOLOGICAL COMPARATIVES, COMMUNICATION AND DEVELOPERS' TOOL KIT

BACKGROUND

Currently recreational wearables such as a Fitbit and others which are designed for the weekend or recreational athlete. These products are not only inaccurate but are not designed for professional sports, Olympic sports, college sports and high school sports. It is obvious to anyone who understands the vast arrays of sports that all land sports, ball sports, and water sports are included.

In addition, current technology and current product designs are limited and do not account, for the measurement of a player's physiological characteristics as a comparative to the player's performance. It is obvious to anyone familiar with the art that more than one player's physiological characteristics and performances could be measured and analyzed. It is also understood that more than one athlete could constitute the definition of a team sport.

In addition, it is also understood that biosensors sampling involves simple and non-invasive collection methods which allow easy and fast diagnostic testing. Oral cavities contain salivary secretions, an abundant blood supply, lymph nodes, ingested pathogens, ingested toxins, ingested allergens, ingested drugs, ingested nutrients, and/or ingested food constituents. Biosensors located in the oral cavity, chest, ear, mouth, eye, neck, face, leg, arms, back, foot for example are not currently networked and capable of comparing biosensor data with performance data.

The presence of various biomarkers permits accurate reflection of normal and disease states in animals and humans. Information derived from the oral cavity is capable of augmenting, or possibly replacing blood sampling, and/or oral cavity information may be used as an efficient precursor before other more invasive medical diagnostics are employed. However, currently available methods for the detection of various biomarkers are inefficient and do not alert or communicate information derived from biomarkers contained when networked in a rapid manner. Currently a network of biosensors, sensors, and devices which measure activity are not capable of alerting an array of data required and useful to coaches, trainers, players and managers of serious individual or team sports.

A sports wearable network designed for serious athletes, for accurate health information gathering, assessment, monitoring, and ultimately, improved athletic performance and training and assistance and intervention when an athletics biomarkers are beyond the safe zone or optimal performance zone is currently not addressed.

In addition, currently there is a profound lack of integration between a multitude of cross-linked technologies and skills when determining information regarding metadata diagnosis; with geometric tracking, multimedia, communication networks, analytics, alerting, and kinematics for individuals, team sports, organizational groups, animals and humans, which enhance health and performance. In addition, these current limitations restrict a multi-dimensional approach which could seamlessly measure individuals and animals with greater accuracy, convenience, yet far less intrusively. In addition, the lack of integration between disciplines fails to address the growing need for the next level of metadata and biological tools which could provide early detection of an athlete's health, early warning signs of dehydration, heart problems, past concussions, and other medical issues. Furthermore, the lack of integration of bio-stats when compared to a players or team performance does not balance an athlete's skills with their real-time health. Thus coaches today are in the dark when it comes to pushing his or her athletes and balancing training and fitness with exertion and physical limitations. The current invention balances both performance with physical limitations for both humans and animals, i.e., racehorses etc.

A smartbit definition could include one or more biosensors, accelerometers, gyroscopes, wireless communication protocols (wifi, etc.) located on or embedded any tack. Tack is defined as a piece of equipment or accessory equipped on horses in the course of their use as domesticated animals. Saddles, stirrups, bridles, halters, reins, bits, harnesses, martingales, and breastplates etc. are all forms of horse tack. Equipping a horse is often referred to as tacking up.

In addition, a plurality of biosensors can be integrated with various geometric models, visualization, complex spatial-temporal relations, human and animal facial and physical relationships (individually and group), data associations (i.e., pixels, auditory, motion, optimum breathing, oral airflow, accelerometers, accelerometer arrays, tri-axial accelerometers, gyroscopes, tri-axial gyroscopes, pressure sensors, magnetometers, goniometers, inertia-sensor, tracking, XYZ locators to determine the player's precise location of the horse on a horse race track, show horse competition field, riding path, or any geography the horse travels and moves.

In addition, the present invention includes metabolic biosensors which can be embedded on the animal's body or equipment, attached on the body or equipment. In addition, high-definition video capture, body wearable sensors, RFIDs, readers, positioning, micro- and nano-electronics, micro- and nano-enabled energy harvesting, micro- and nano-energy storage, micro- and nano-devices micro- and nano-timer, micro- and nano-devices, micro- and nano-programmable processors, micro- and nano-memory, micro- and nano-integrated power management, micro- and nano-programmable hardware, micro- and nano-wireless communication capabilities across multiple, various degrees of dynamic alerting, tracking, positioning, multi-media, analytics, time tracks, historical and other comparative data inputs, communications and platforms etc.). Collectively, these inputs can be synced and integrated with all forms of data capture. The wearable sports system can provide important real-time or near time analytics in order to correct or modify motion, behavior for individuals, team sports or organizational groups for equine, pets, and other animals and humans.

Furthermore, equine sports equipment do not include embedded or attached wearable bio-measurements and performance technologies. Thus racehorses, show horses, recreational horse owners and trainers are left with instinct and personal knowledge when training horses. To make it worse, thousands of horses are injured and destroyed every year. The present invention undoubtedly provides equine owners and trainers what will become essential information regarding the horses short-term and long-term health. The present invention will describe and detail the present invention's many applications as it applies to the equine industry and as it relates to animals cruelty and abuse through lack of knowledge. Real-time or near-time knowledge when standardize and widely used will lessen abuse and will enable authorities world-wide to thereafter concentrate on intentional animal abuse rather than unintentional. It is obvious to anyone familiar with the art that the present invention could be utilized for all animals in addition to equine. For example, dog racing, show dogs, military dogs, see and eye dogs, police dogs, etc. In addition, it is obvious to anyone familiar with the art that the present invention also includes all animals which purpose in life is recreational.

Humans and animals at times have a different metabolism and genetic code however walk together, play together, play sports together and are sometimes judged or timed in one or more sports synonymously.

However, the present invention could benefit pet owners with a great deal of health information.

The definition of asynchronous as it relates to the present invention requiring a form of computer control timing protocol in which a specific operation begins upon receipt of an indication (signal) that the preceding operation has been completed.

The definition of synchronous as is relates to the present invention is existing or occurring at the same time.

SUMMARY OF THE INVENTION

The present invention provides smart wearable devices, systems and methods relating thereto, as well as auxiliary devices and methods, for greatly improving animals and human well being, sports performance and physiological set-points through innovations in such technologies. The invention combines its enhanced, "smart", sensor devices and methods with communications, software management, data management, instant and long term animals and human analyses, multimedia inputs, visualizations, geometric motion, tracking, kinematics, alerting, therapeutic, electronic medical records and other beneficial systems not previously available.

The Wearable Sports System (WSS) of the invention provides for communication systems and alerting technology that link a multitude of biological information inputs together. This method of gathering biological information from wearable devices provides the basis for a real-time or near-time snapshot of an animal or human's optimal sports performance and physical limitations.

Accordingly, a sensor alerts and communication system, methods and devices related to and used in conjunction therewith are provided which address the needs and provide the advantages outlined herein.

Also the present invention provides Sports Guidance Technologies (SGT) device according to the invention where sensor devices are networked together in response to alerts and/or signals from the wearable sports system.

In an aspect of the invention, a device is provided which includes a smart sensor receptacle for a sensor. SGT imbedded wearable sensors could be utilized including, but not limited to high level sports performance, animal sports and recreational performance, and other medical diagnostics, and analytics function. The device includes one or more sensors contained within or upon the receptacle or multiple receptacles networked and communicated to mobile device (smartphone, tablet, etc.) used for example by trainers and coaches or athlete themselves.

In another embodiment of the invention, the wearable sports system can streamline and integrate performance measurements such as, but not limited to, various geometric models, visualization, complex, spatial-temporal relations, human and animal facial and physical relationships (individually and group), data associations (i.e., pixels, auditory, motion, optimum breathing, oral air-flow, accelerometers, accelerometer arrays, tri-axial accelerometers, gyroscopes, tri-axial gyroscopes, pressure sensors, magnetometers, goniometers, metabolic biosensors, high-definition video capture, body-wearable sensors, RFIDs, readers, positioning, micro- and nano-electronics, micro- and nano-enabled energy harvesting, micro- and nano-energy storage, micro- and nano-devices, micro- and nano-timer, micro- and nano-devices, micro- and nano-programmable processors, micro- and nano-memory, micro- and nano-integrated power management, micro- and nano-programmable hardware, micro- and nano-wireless communication capabilities across multiple, various degrees of dynamic alerting, tracking, positioning, multi-media, analytics, historical and other comparative data inputs, communications and platforms etc.). Collectively, these inputs can be synced and integrated with all forms of data capture. The wearable sports system can provide important real-time or near time analytics in order to correct or modify motion, behavior for individuals, team sports or organizational groups for animals and humans.

In a further embodiment, the invention provides a wearable sports system including the above-described smart receptacle, one or more sensors contained within, attached, or upon the receptacle and at least one interface with a network configured to utilize the information obtained from the one or more sensors.

It is understood by anyone familiar with the art that independent to wireless storage, the data could be stored in any SGT device through any digital storage device, connector, or mechanism.

The invention provides, in another embodiment, a system which includes a device configured to be inserted or attached to an animal or human. The device includes a smart sensor receptacle for one or more sensors wherein the receptacle is selected and could be customized for any human or animal condition. For example, the receptacle can be selected from the group consisting of a horse-bit, a thermometer, a receptacle configured so that it cannot be swallowed, a receptacle for babies or adults with biosensors on one side and a RFID on the other side which is on the outside of a mouth, a customized teeth retainer which could be attached to a sports guard to enhance functionality and purpose, a receptacle to be attached to a human or animal body, an insert in a gum, an attachment to socks, shoes, hats, wristbands, headbands helmets, goggles, ear modules, clothing, eyewear, etc.

The bridle consists of the following elements:

Crownpiece: The crownpiece, headstall (US) or headpiece (UK) goes over the horse's head just behind the animal's ears, at the poll. It is the main strap that holds the remaining parts of the bridle in place.

Cheekpieces: On most bridles, two cheekpieces attach to either side of the crownpiece and run down the side of the horse's face, along the cheekbone and attach to the bit rings. On some designs, the crownpiece is a longer strap that includes the right cheek and crownpiece as a single unit and only a left side cheekpiece is added.

Throatlatch: the throatlatch (US) or throatlash (UK) is usually part of the same piece of leather as the crownpiece. It runs from the horse's right ear, under the horse's throatlatch, and attaches below the left ear. The main purpose of the throatlatch is to prevent the bridle from coming off over the horse's head, which can occur if the horse rubs its head on an object, or if the bit is low in the horse's mouth and tightened reins raise it up, loosening the cheeks.

Browband: The crownpiece runs through the browband. The browband runs from just under one ear of the horse, across the forehead, to just under the other ear. It prevents the bridle from sliding behind the poll onto the upper neck, and holds multiple headstalls together when a cavesson or second bit is added, and holds the throatlatch in place on designs where it is a separate strap. In certain sports, such as dressage and Saddle seat, decorative browbands are sometimes fashionable.

Noseband: the noseband encircles the nose of the horse. It is often used to keep the animal's mouth closed, or to attach other pieces or equipment, such as martingales. See also Noseband.

Cavesson also called Caveson or caves[s]on noseband, is a specific type of noseband used on English bridles wherein the noseband is attached to its own headstall, held onto the rest of the bridle by the browband. Because it has a separate headstall (also called slip-head), a cavesson can be adjusted with greater precision; a noseband that is simply attached to the same cheekpieces that hold the bit cannot be raised or lowered. In Saddle seat riding, the cavesson is often brightly colored and matches the browband. Variations on the standard English-style bridle are often named for their style of noseband. For use in polo, a gag bridle usually has a noseband plus a cavesson.

Frentera, a strap running from the browband to the noseband, primarily seen on bridles of certain South American design Fiador, a form of throatlatch, is used with a hackamore.

Reins: The reins of a bridle attach to the bit, below the attachment for the cheekpieces. The reins are the rider's link to the horse, and are seen on every bridle. Reins are often laced, braided, have stops, or are made of rubber or some other tacky material to provide extra grip.

Bit: The bit goes into the horse's mouth, resting on the sensitive interdental space between the horse's teeth known as the "bars."

On a double bridle, where the horse carries two bits (a curb and small snaffle, often called a "bit and bradoon"), a second, smaller headstall, known as a 'bradoon hanger' or 'slip head' is used to attach the bradoon. A second set of reins is attached to the bradoon, and hence the rider carries tour reins.

The bridle, depending on style, may also contain some of the following elements:

Bit guards: Bit guards are optional fittings used on some bits.

Curb strap or curb chain, used primarily on bridles with a curb bit, a small strap or chain, usually flat, that runs from one side of the bit to the other, and puts pressure on the chin groove when curb reins are tightened.

Lip strap: a small strap used on a few curb bit designs, attaches between the bit shanks of a curb bit at the halfway point, used to keep the curb chain properly positioned and may prevent the horse from grabbing at the shanks with its lips.

Bit hobble: basically, a curb strap used on the snaffle bit rings of a western bridle. Provides no leverage, but because open-faced bridles have no cavesson to prevent the horse from gaping its mouth open, it prevents the bit rings from being pulled through the mouth if strong pressure is applied.

Shank hobble: A strap, bar or chain that connects the shanks of a curb bit at the bottom of the bit. Serves to stabilize the bit, prevent a lasso or other object from being caught on the shanks.

Winkers or blinkers, also called "blinders", are partial eye blocks used primarily on driving horses and some race horses that prevent the animal from seeing what is behind it.

Overcheck, also called a bearing rein or "check rein," is a specialty rein that runs from a snaffle bit, past the crownpiece, along the crest of the neck, and attaches to the front of a harness on a driving horse. It prevents the horse from dropping its head too low. Overchecks are also sometimes used on riding horses, especially ponies, to keep them from grazing while being ridden by a small child who may lack the physical strength or skill to raise the animal's head up.

Ornaments such as phalerae and sallongs.

It is understood by anyone familiar with the art that there are hundreds of design variations, the basic families of bits are defined by the way in which they use or do not use leverage. They include:

Direct Pressure Bits Without Leverage:

Snaffle bit: Uses a bit ring at the bit mouthpiece to apply direct pressure on the bars, tongue and corner of the mouth.

Leverage Bits:

Curb bit: A bit that uses a type of lever called shank that puts pressure not only on the mouth, but also on the poll and chin groove.

Pelham bit: A single curb bit with two sets of reins attached to rings at the mouthpiece and end of the shank. Partly combines snaffle and curb pressure.

Kimblewick or Kimberwicke: A hybrid design that uses a slight amount of mild curb leverage on a bit ring by use of set rein placement on the ring.

Bit Combinations

A type of bridle that carries two bits, a bradoon and a curb, and is ridden with two sets of reins is called a Weymouth or double bridle, after the customary use of the Weymouth-style curb bit in a bridle.

Non-Curb Leverage Designs:

Gag bit: A bit that, depending on design, may outwardly resemble a snaffle or a curb, but with added slots or rings that provide leverage by sliding the bit up in the horse's mouth, a very severe design.

In-hand bits are designed for leading horses only, and include the:

Chifney Anti-Rearing Bit: This is a semi-circular-shaped bit with three rings and a port or straight mouth piece used when leading horses. The port or straight piece goes inside the mouth, and the circular part lies under the jaw. The bit is attached to separate head piece or the head collar and the lead is clipped onto the bit and headcollar to limit the severity.

Tattersall ring bit, Horse-shoe stallion bit

Bits are further described by the style of mouthpiece that goes inside the horse's mouth as well as by the type of bit ring or bit shank that is outside the mouth, to which the reins are attached.

In communication networks, a node (Latin nodus, 'knot') is either a connection point, a redistribution point, or a communication endpoint (e.g. data terminal equipment). The definition of a node depends on the network and protocol layer referred to. A physical network node is an active electronic device that is attached to a network, and is capable of creating, receiving, or transmitting information over a communications channel.[1] A passive distribution point such as a distribution frame or patch panel is consequently not a node.

In one embodiment of the present invention includes biosensors to attach or be embedded with all equine equipment including but not limited to:

The saddle: Saddles also have their own accessories such as crupper, breeching, surcingle and breastplate.

Reins: are designed to facilitate better communication between the horse and the rider. By pulling left or right you can tell the horse were you want him to go. Pulling both reins at the same time will signal the animal to stop.

Headgear: will enable you to control the horse. There are several accessories worth mentioning here, including headcollar—with the headstall and nosebands—bridle and halters.

Stirrups: this piece of equipment hangs on the side of the horse. It is basically the support for the rider's feet. Artificial Aids: Mechanical means by which the rider conveys his wishes to the horse. Includes spurs and whip.

SGT device can include any combination of biosensors and RFID tags, micro- and nano-electronics, micro- and nano-enabled energy harvesting, micro- and nano-energy storage, micro- and nano-devices, micro- and nano-electronics, micro- and nano-enabled energy harvesting, micro- and nano-energy storage, micro- and nano-devices, micro- and nano-timer, micro- and nano-devices, micro- and nano-programmable processors, micro- and nano-memory, micro- and nano-integrated power management, micro- and nano-programmable hardware, micro- and and nano-wireless communication capabilities across multiple frequencies located in the mouth or integrated outside of a mouth. In addition, other consumer products could include a subscription database with software analytics which measure a player's performance as it matches and relates to his or her physiological analysis.

In yet a further embodiment of the invention, a method is provided for obtaining sensor data from a human and/or an animal. The smart receptacle contains or receives within or upon it one or more sensors capable of providing information relevant to the health or a physiological characteristic of the human or animal. The method further involves activating or monitoring the one or more sensors to obtain or analyze the information relevant to the health or a physiological characteristic of the human or animal and transmitting at least some portions of the health or physiological information or analysis to a network capable of utilizing the information obtained.

The recognition component in these systems and methods of the invention, often called a receptor, can use, e.g., biomolecules from organisms or receptors modeled after biological systems to interact with an analyte of interest. This interaction can be measured by a biotransducer which outputs a measurable signal proportional to the presence of a target analyte in the sample.

In another aspect, of the method of the invention, the receptacle used in the above method includes, a smart sensor receptacle for one or more sensors for example, but not limited to, a retainer combination sports guard, an attachment to a tooth, an attachment to an animal or human body, an insert in a gum, socks, shoes, hats, wristbands, headbands, helmets, goggles, ear modules, clothing, eyewear, etc., inserts with biosensors, sensors, communication capabilities including but not limited to camera, audio, thermal IR, multi-media, speakers, a RFID, etc. on the inside or outside of a mouth and an animal toy which is configured not to be swallowed, securely and strategically placed touching a body or within an animal's or human's oral cavity, eye cavity, ear cavity and nose cavity.

In yet an additional aspect, the invention includes a wearable sports system for an animal or human. The wearable sports system includes a smart, wearable or attachable device. The smart, wearable, attachable or externally insertable device is configured to obtain information from, provide information to, or both, the one or more sensors located on the body or within the aforementioned cavity receptacle. And, the one or more sensors or the smart, external device, or both, are configured to transmit the information to a network.

Also provided is a customizable development tool kit or platform for multiple SGT purposes and functions and for building a wearable sports system to provide information, analysis or alerts for an animal, animals, human or humans, comprising a kit or platform of customizable components to meet the needs of a developer, consumer or user of the system, the components comprising at least one sensor inserted or attached to the animal, animals, human or humans, at least one receptacle configured to contain or receive the sensor, and at least one network unit configured to receive information, analysis or alerts from or transmit information, analysis or alerts to the at least one sensor and analyze, transmit, or both, the information, analysis or alerts obtained or received, wherein components for selecting the sensor receptacles, the sensors, and the network units are made available to the developer, consumer or user to construct, or have constructed a system configured to obtain or transmit information, analysis or alerts customized to meet the specific needs of the developer, consumer or user.

In addition, the SGT device could utilize the network of wearable devices to guide and train individual or teams. For example, a vibration on the upper right arm when a player needs to pass the ball to another player to the right side of him. It is obvious to anyone familiar with the art that coaches and trainers could manually activate one or more vibrations or other mechanisms to signify directions or signals, ball handling and an athlete's timing and mechanics. Furthermore, it is obvious that the coach or trainer could distinguish for example the strength of the vibration or location of the vibration to signify the movement of a player, rotation, arm movement, ball, bat, hockey stick in any direction.

In yet another embodiment, the SGT network could activate one or more wearables not only to define a player's exact motion but also to correct, the player's motor skills and make adjustments when needed to optimize a player's or teams' performance.

In yet another embodiment, wearable sports system can be employed to compare the performance and kinematics of an individual player with the advanced player in order to pinpoint the areas of development for the individual. For example, back-hand stroke angular motion and stroke power could be greater in advanced tennis player due to their use of efficient kinetic chains.

In addition, automatic SGT artificial intelligence rather than the coach could be customized to help directionalize the player's arm movement when throwing a ball, catching a hall or for any and all sports activity. For example, the SGT artificial intelligence could analyze and scan a player's body and body parts. The system, can determine the most efficient motion for the player when pitching a fast ball for example and correct or adjust his motion through the vibration or tightening the wearable to help direct the muscles needed to throw the ball. Visualizing the exact movements of a golf swing for example through virtual three dimensional images can help translate it into reality for the player. It is obvious to anyone familiar with the art that all sports have optimal motion and optimal mechanics which are refined through repetitive training sessions. In one embodiment of the present invention wearable could assist and guide an athlete whether in an individual sport or a team sport.

In another embodiment of this invention, any type of robotics, including, but not limited to, airborne, water, land robotics and others can be used in sports training. For example, GPRS drone locators can be placed in the practice vicinity (air, water and land etc.), and can film, monitor, track and guide each player on the field through the wearables that the player puts on. Robotic can work as a coach, trainer, player or assist, etc. A portion of the body of the robotics (arms, arm sleeves, leg sleeves, head, skull, face, upper-back, lower back, legs, knees, shoulder, elbow, hip, ankle, armpit, hand, glove, foot, toe etc.) can also be employed in training. For example, robotic sleeves with embedded artificial intelligence which automatically calculates the angle, velocity and strength, etc. of shooting based on the physical characteristics of the basketball player can be used to train shooting and improve the free throw percentage.

In another embodiment of this invention, coaches or trainers could be replaced by a software program or artificial intelligence. Data from wearables, sensors on sports equipment, environmental sensors, and data entered about the athletes' health and historical performance data, could be used to assist in training. This could enable athletes training and increase their skills when trainers are not available.

In another embodiment of this invention, the SGT device could function as a coach and trainer to enhance an athlete's performance. Smart clothing and smart equipment could assist in determining exact movement, strength, bounce, throw, etc. These smart clothing and equipment could further assist in determining how to improve any athlete's performance and act as a guide, coach, or trainer. This smart coach could guide by use of all physiological senses and perceptions including ophthalmoception, audioception, gustaoception, olfacoception or olfacception, tactioception, (thermoception), kinesthetic sense (proprioception), pain (nociception), balance (equilibrioception), vibration (mechanoreception), and various internal stimuli (e.g. the different chemoreceptors), tension sensors, pressure, stretch receptors, time perception and other beneficial systems not previously available. The intensity of these senses and perceptions input could be used to guide differently.

In yet another embodiment of the present invention, wearables could be used by the player to adapt to environmental conditions such as noise level, humidity, altitude, environmental temperature, precipitation, humidity, distance, wind speed and direction, hill slope and height, soil and sand conditions, grain, grass type and height, icy conditions, raining conditions, slippery conditions etc. by adjusting the player's movements, for example, to take smaller more deliberate steps or pass the ball further in response to a 10 mile an hour wind from the northwest (NW). The SGT device could calculate and logistically guide the player to adjust his or her pass, hit or kick to counter the wind factor or any weather related or environmental conditions.

In another embodiment of the present invention, the artificial intelligence could guide one or more players through a combination of kinematics, high definition video, animation, facial and body recognition to determine precision movements and the exact measurement of a player's touch of a ball for example.

In another embodiment of the present invention, the convergence of wearable technologies enables coaches and referees to better determine fouls when video camera is not taken at the right angle or angles and enables coaches to review computer animation and precise movement as it relates to other players, logistics and precision location.

In yet another embodiment of the present invention wearable(s) could contain impact sensors, motion sensors, gyroscopes, tri-axial gyroscopes, accelerometers, accelerometer arrays, tri-axial accelerometers, pressure sensors, magnetometers, goniometers and XYZ locators to determine the player's precise location on the sports field. It is obvious that all part of the athlete's body could utilize wearables through the SGT device to detect exact movement on the location for example of the arm or arms or any other body part.

In another embodiment of the present invention, wearable sports system (WSS) which networks all body sensors can be used to estimate whole body center of mass, whole body velocity and acceleration real time or near time in the field with full body modeling. For example, when the acceleration of the whole body center of mass is measured, phases of the stroke cycle in which propulsive forces are not being applied effectively and the body encounters great resistance can be identified and linked to the technique of the swimmer to improve performance.

In another embodiment of the present invention, wearable sports system can be applied to quantify an individual's movement patterns during athletic maneuvers in order to increase the probabilities of identifying those at increased risk of injuries.

In another embodiment of the present invention, kinematic data obtained using SGT device can assist, in the choice of equipment such as balls, bats, rackets, clubs and tees, etc. For example, there are different types of racket which vary in mass, swing weight and twist weight etc. Utilizing different types of racket could result in changes in shoulder joint power, internal/external rotation peak moments, and activities in latissimus dorsi muscles etc. during acceleration and follow through phase. This information is essential to quantify the loads on the body during play in order to improve the performance and reduce injuries.

In another embodiment of the present invention, smart balls, hoops, bats, rackets, clubs and tees, etc. could embed a smart chip to precisely determine movement, rotation and placement with great accuracy.

In another embodiment of the present invention, a player's physiological range through biosensors could be predetermined and customized. For example, a player's setpoint range of temperature when resting is 97° F. (36.1° C.) and when active 99° F. (37.2° C.). Another example, a player's resting heart rate is 60 beats per minute and his optimal performance heart rate is 134 beats per minute. The SGT device could be programmed to alert coaches when one or more player's heart rate is too high and exceeds his or her optimal range.

In another embodiment of the present invention, data acquisition mode of the wearable sensors can be changed automatically based on the predetermined set points so as to better characterize emergency or unusual situation. For example, when an accelerometer in the helmet or mouth guard of a football player exceeds a specified threshold during play, alert and faster data acquisition can be automatically triggered. Data can be collected at a much faster speed in order to evaluate possible concussive impact where rotational acceleration and rotational velocity could be largely increased. The alert can activate other sensors or biosensors such as heart rate, respiration rate, blood pressure sensors, etc. to acquire data at faster acquisition modes as well.

In another embodiment of the present invention the wearable sports system could alert coaches when a player's performance is suboptimal due to dehydration, heat-shock, illness, lactic acid build-up in muscles, lack of energy due to diet, or others. The wearable sports system enables coaches and trainers the ability to compare performance with a player's physiological attributes and thus know when to give him more play time or remove him from a game.

It is obvious to anyone familiar with sports that optimal performance is analyzed by historical data and varies from player to player and from time to time.

In another embodiment of the present invention, the wearable sports system and SGT device database can track and analyze, compare and report performance in any activity or sport as it relates to physiological measurements.

In yet another embodiment, the wearable sports system and SGT device could analyze not, only individual comparative (physiological, environmental, performance, kinematics) but also a team composite of energy levels.

In yet another embodiment of the invention, an athlete such as mountain climber, marathon runner, safari, hunter, et al. when injured might not be able to communicate to rescuers about their injuries and/or location. In such circumstances, tracking wearables and physiological analytics could work in unison and communicate the athletes' injury and health status and exact location. This could save lives and assist paramedics to prepare well for injuries of injured athletes.

In another embodiment of invention, SGT device offers a way for those talented athletes who may suffer from non-disabling diseases or injuries to participate in and perform well in team and professional sports. Vivian is very talented basketball player but suffers from a heart arrhythmia. She takes medication for her disease and is in care of a cardiologist. Her disease does not negatively impact her daily life. However, she is unable to play in her school team due to her heart conditions. SGT device could network in real time her wearables to measure her heart function, blood oxygen levels, and, perhaps, even her blood medication levels to alert coach when she needs to rest and thus be replaced for short periods of time or to change her role in her team in real time to avoid precipitation of her symptoms and cause harm. Similarly, Jake who is a very talented football player has injured his leg. He is recovered but his muscles are still weak so his injuries could change his when the muscle is fatigued. SGT device could assist the coach to remove him when his is not proper and makes him susceptible to fall, so he can rest his leg and get medical treatment if needed. This could prevent further injuries to Jake without hindering his and team's success. It is understood by anyone familiar with the arts that out invention can be used in many such situations for several different sports in assisting athletes, coaches, and physicians to participate in sports and perform to best of their capacities without compromising their health.

In another embodiment, the present invention (SGT tool kit) enables humans to measure not only the animal's and human's metabolism, calories, biometrics, and motion but enables humans when performing one or more tasks the ability to compare his or her biometrics with the animals.

The software application can in real-time or near-time compare the analytics of the animal (horse, dog, etc.) such as but not limited to calories expended, SpO2, internal temperature, heartrate, pulse, and other biometrics with its human counterpart. For example, a horse's biometrics results can be compared to a human's biometrics results when the human is riding the animal. In this example, the horse's SpO2, internal temperature, heart rate, EMG, impact, GPS and GPRS, pressure and other biometrics and wearable sensors can be analyzed to compare and contrast how the ride affected the human's biometric levels and vice-versa. The resulting contrast and comparative could greatly assist the human's knowledge in the his or her ability to adjust to the horse or how the human can influence and train the horse to better adjust to the rider.

In an embodiment of the present invention also allows the biometric comparison in real-time or near-time to various SGT toolkit applications in order to digitally transmit and receive both the animal and human biometrics and analytics.

In another embodiment, various biometric measurements, sensor and physiological measurements can be accessed through one or more mobile devices in order to compare various timestamped results from the human and animal in real-time, synchronous, near-time asynchronous.

In addition, the SGT tool kit as previously described utilize various analytics, graphics based on the human and animal comparative and contrast.

In another embodiment, not only internal biometrics between animal and humans can be measured through various sensors but the shared environmental condition when riding a horse or when walking or running with a dog can be measured and compared. Other comparatives between one or more humans and animals could also be measured logged and its historical results analyzed.

Another embodiment includes communicating and alerting the human when either the animal or human's biometrics reach a certain level based on one or more physiological set-point or set-points.

The communication of physiological comparatives between humans and animals can be accessed on mobile devices, information and wireless communication i.e., Bluetooth etc., transmitted on the API, gathered by various software applications, customized to the animal, human and task, related through one or more accessories historically logged and accessed privately or publicly.

A linked series of wearables sensors whether attached, worn, in proximity, imbedded or attached can become a physiological component of measurement between animals and their human counterpart.

In addition, in another embodiment GPS/GPRS can track not only real-time or near-time timestamp comparatives between animals or humans but tracking and location variables.

BRIEF DESCRIPTION OF THE DRAWINGS

FIG. 7 depicts embodiments of various types of smart sport guards, in accordance with embodiments the present invention.

FIG. 8 depicts embodiments which exemplify the application of sports guidance technologies in training, in accordance with embodiments of the present invention.

FIG. 9 depicts embodiments which exemplify external integrations through environmental factors, in accordance with embodiments of the present invention.

FIG. 10 depicts embodiments which exemplify internal integrations through physiological measurement in relation to performance, in accordance with embodiments of the present invention.

FIG. 11 depicts embodiments which exemplify predetermined sensor sot points, data collection, alert, and report system, in accordance with embodiments of the present invention.

FIG. 12 depicts embodiments which exemplify graphical representation of sensor predetermined set points, time stamped data collection, alert, and report system, in accordance with embodiments of the present invention.

FIG. 13 depicts embodiments which exemplify kinematic factors to maximize performance through the kinematic identification, analysis, and directional guidance of each player as apart of the external integration of SGT sensors and software, in accordance with embodiments of the present invention.

FIG. 14 is a depiction which exemplifies a set play identified by the wearable sensors which ultimately results in a play for the team to score and improves their own court knowledge of basketball plays as well as their team chemistry with one another, in accordance with some embodiments of the present invention.

FIG. 15 depicts embodiments which exemplify dynamic alerting software and secure networks from wearable sports system, in accordance with embodiments of the present invention.

FIG. 16 depicts embodiments which exemplify utilities of a wearable sports system for racing horse, in accordance with the present invention.

FIG. 17 presents examples of wearable network integrated for performance measurement, in accordance with the present invention.

FIG. 18(a) depicts embodiments which exemplify a wired equine smartbit hardware device in accordance with the present invention.

FIG. 18(b) presents depicts embodiments which exemplify a wired equine smartbit hardware device, in accordance with the present invention.

FIG. 19 depicts embodiments which exemplify an embedded wireless equine smartbit hardware device.

FIG. 20 depicts embodiments which exemplify utilities of the integration of the trainer, jockey and horse with one or more wearables, in accordance with the present invention.

FIG. 21 depicts embodiments which exemplify the communication system between the secure database, mobile device with the equine trainer, horse rider, horse owner and the equine biosensors, in accordance with the present invention.

FIG. 22 depicts embodiments which exemplify the animal's real-time or near-time anatomical and physiological analytics as a comparative to any increment of performance time.

FIG. 23 depicts embodiments which determine an equine's gait, balance and speed guidance through an equine's embedded or attached accelerometer(s) and gyroscopes with the communication system.

FIG. 24 depicts embodiments which exemplify the physiological sensor system which measures an animals biometrics as and relative human timestamp comparatives.

DETAILED DESCRIPTION OF THE INVENTION

Figure 1:
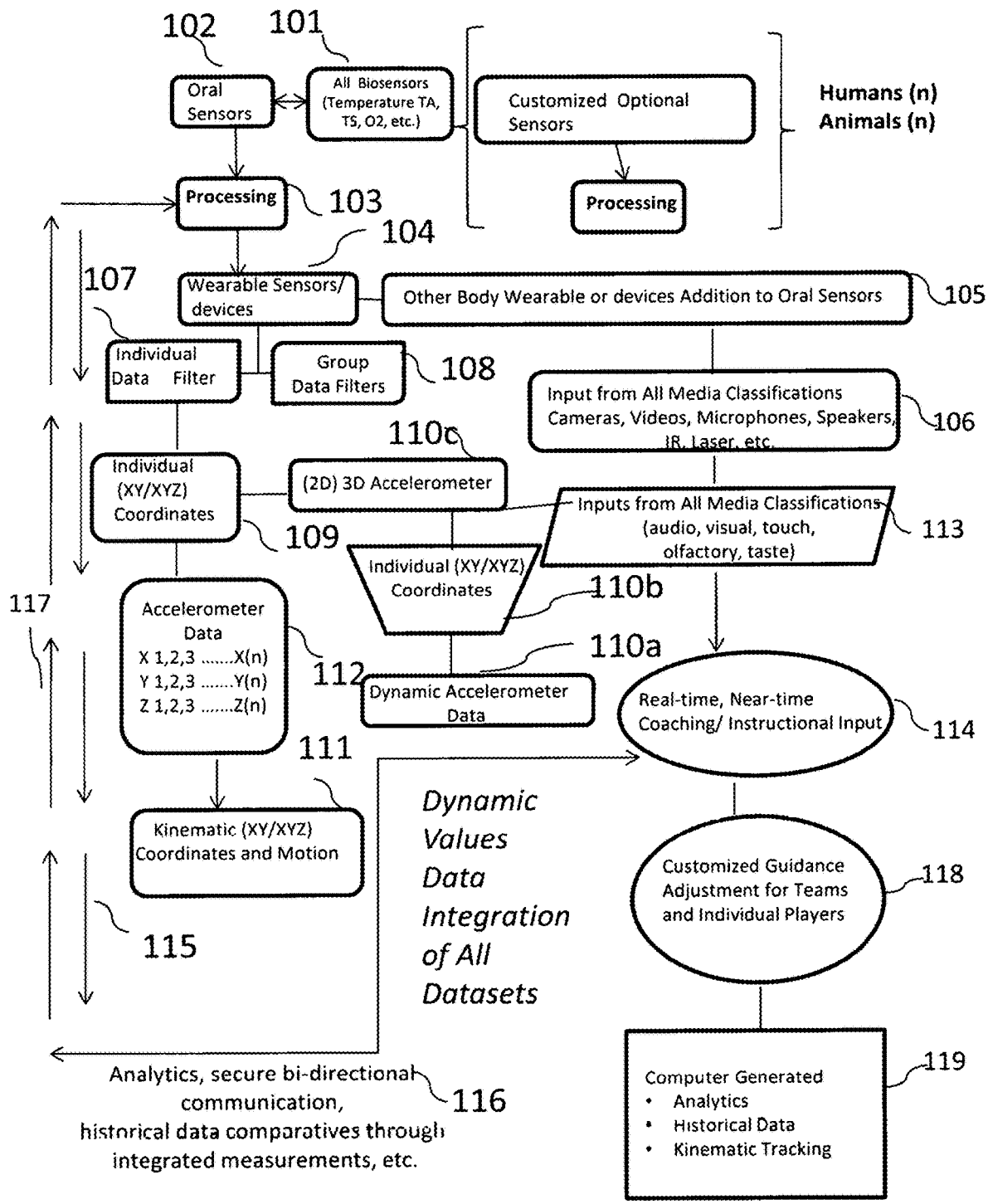
FIG. 1 depicts a block diagram exemplify a wearable sports system which integrates various performance measurements in accordance with embodiments of the present invention.

The foregoing summary, as well as the following detailed description of certain embodiments will be better understood when read in conjunction with the appended drawings. As used herein, an element or step recited in the singular and proceeded with the word "a" or "an" should be understood as not excluding the plural of said elements or steps, unless such exclusion is explicitly stated. Furthermore, references to "one embodiment" or "an embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

As used herein, the term "smart" means a device or object that performs one or more functions of a computer or information system, such as data storage, calculation, Internet access and information transmission.

As used herein the terms "insertable", "implantable", "imbeddable", "embeddable". "temporarily insertable"

"permanently insertable", "temporarily implantable", "permanently implantable", "temporarily imbeddable", "permanently imbeddable", "temporarily embeddable" and "permanently embeddable" refer to means of securely inserting and attaching in or to, or fastening a device, such as being adhered to, cemented, affixed or otherwise securely attached to a surface or object.

As used herein, the term "receptacle" refers to a device or container that receives, retains, has within, or holds something.

Described in its broader respects, the wearable sports system of the invention includes a device configured to be inserted or attached to an animal or human comprising a smart sensor receptacle for a sensor, the device further comprising one or more wearable sensors contained within or upon the receptacle, and at least one interface with a network configured to utilize the information obtained from the one or more sensors or from one or more platforms.

The system as described above may provide one or more functions of the device selected from the group consisting of providing sports function, health analytics, diagnostic analytics, performance analytics; integration of wearable sensors, health-devices, sports and performance sensors on inanimate objects and sports equipment; sports gear, clothing, stadium, ballpark, park; gym, gymnasium, arena, dome, bowl, circus, coliseum, colosseum; customizable developers' tool kit for biosensors, sensors, performance, medical analytics, oral and systemic body diagnosis; integrated, pre-integrated and post-integrated, platforms; any type of medium, secure bidirectional media, multiple media, video, audio, 3D, printing, reporting, analytics, reporting, metadata diagnosis, with geometric tracking, communication networks, analytics, alerting, kinematics for individuals, team sports, organizational groups, animals and humans, communications, software management, data management, instant and long term animal and human analyses, multimedia inputs, visualizations, geometric motion, tracking, kinematics, alerting, therapeutic, historical analysis, time stamped data, reporting and feedback, positioning, the integrated video can be synced with all wearables and other biosensors in order to produce computer-generated precise movement and greater precision or analytics.

The sensors in the provided devices can include, e.g., sensors of blood pressure, core body temperature, heart rate, levels of a predetermined biologic, chemical or medication or their metabolites, sensors to measure a physical property, including one or more sensors which measure a physical property including or consisting of temperature, blood, pressure, teeth pressure, ionic conductivity, airflow, images, optical density, alterations to the oral cavity, surrounding muscle tone, muscle weakness, heart rate, heart rhythms, respiration rate, accelerometer, accelerometer arrays, tri-axial accelerometers, gyroscopes, tri-axial gyroscopes, pressure sensors, magnetometers, goniometers, spectrophotometry, electromagnetic spectrum, gamma waves, X-ray waves, ultraviolet waves, visible waves, infrared waves, terahertz waves, microwaves, radio waves, electrical waves, sound waves, magnetic waves, ultrasonic waves, magnetic resonance, magnetic field, electro- or magnetic-encephalography, functional magnetic resonance imaging, optical topography, global positioning or tracking, accelerometer activity, gyroscopic activity, kinematic activity and radiation wave activity.

Generally, the system can include a historical database of the animal or human as to one or more characteristics from which comparisons or analyses are configured to be made, or a database of animals or humans having a common characteristic to the animal or human on which the smart device is located and for which a predetermined comparison is configured to be made.

The system can include a database compilation of one or more players' biological or physiological attributes as they relate to one or more players' performances.

The system can include a database compilation of one or more players' kinematics as they relate to one or more players' performances.

The system can be configured to analyze individual or team sports performance as it, relates to various body components and sensors.

Specific examples of the system include: the smart sensor receptacle is a head band and the smart sensor receptacle is configured with WiFi connectivity, the system further includes one or more sensors for temperature or acceleration, the system further comprises tracking and precision field logistic software, a digital transactional communication interface and controls, navigation and operational, guidelines configured to facilitate performance, the system further provides an alerting signal when outside a pre-set range; the smart sensor receptacle is an arm band with full connectivity, the system further includes full server access and is configured for an analytical processing capability; the smart sensor receptacle is a full or partial retainer, the system further includes a smart mouth guard accessory, the one or more sensors includes sensors for temperature or oxygen levels, the system is further configured with WiFi connectivity and is configured to provide an alerting signal when outside a pre-set range; the smart sensor receptacle is an ear bud, the system is provided with full connectivity, full server access and is configured for an analytical processing capability comprising performance analysis.

The system can include software configured to provide athletic analysis, logistics, specialty location XYZ modules, and date entry timestamp and input.

The system can include smart data compiler software configured to data stream information for use by the user to evaluate one or more player's performances when playing in a sport or requiring an athletic performance.

The system can be set up for use with an individual to obtain information from the individual and transmit it or analysis derived from it directly or indirectly to a network.

The system network can interface with a mobile device which in turn provides sensor information or analysis to an individual user, who then receives information feedback regarding a physiological characteristic of a current activity he is engaged in, such as running, jogging, walking, or a physical characteristic involved with playing a sport.

The system includes one or more network units which can be configured to carry out a functionality selected from the group consisting of signaling bi-directional transmissions to a secure server through one or more of WiFi, Bluetooth, GPS, NFC or other wireless means, temporarily storing information in the smart device, bi-directionally transmitting alert to pre-selected devices or pre-selected personnel.

The network units of the system include one capable of utilizing the information obtained from the one or more sensors and having functions including, but not limited to, data storage, data retrieval, data synthesis, alert programs, data management, characterization, filtering, transformation, sorting, processing, modeling, mining, inspecting, investigation, retrieval, integrating, dissemination, qualitative, quantitative, normalizing, clustering, correlations, computer derived values and ranges, simple or complex mathematical calculations and algorithms, statistical, predictive, integrative, interpretative, exploratory, abnormality seeking, data producing, comparative, historical or previous from same or different individual or team, visualizing or presentation development platforms.

The network units included in this aspect, include, but are not limited to, one or more of measurements of performance, measurements of health, measurement of energy level, measurement of physiological attributes, information obtained from sensors, kinematics information, information obtained from cameras, information from sensors inserted or attached to body parts, information from instruments used to measure performance, information received from sensors attached to or associated with inanimate objects and sports equipment.

The system may utilize a network configured to analyze one or more performance parameters of a player or teams. Additionally, the network can be configured to analyze a composite input of a plurality of team or group members.

The system may utilize a network which provides means by which one or more sensors are activated by another sensor, device or remote controller.

The system may utilize a network which provides means for integrating one or more wearable sensors with sensors attached to or associated with inanimate objects or sports equipment.

In one embodiment, a method of training which utilizes the system and devices described as part of wearable sports system as laid out in this application is provided. The method includes the steps of providing a virtual presentation of one or more athletes for visualization by one or more users.

In the above-described method, virtual presentation is configured to be three-dimensional profiles customizable by one or more users to facilitate performance.

In a particular aspect of the above method, one or more data servers are provided for the user to virtually display three-dimensional profiles of one or more bodies or limbs for precise movement and analysis.

In another aspect of the above method, a controller is provided with the capacity to configure the database of one or more sensors and predetermined set points, scale, type of sport, athlete, individual energy alerting, team energy alerting, physiological computations, historical references, search engine and analytics.

In another aspect of the above method, an analytical processing capability comprising motion and performance comparison is provided.

In a further aspect of the above method, virtual presentation of one or more athletes comprises a holographic images and patterns of synced simulations through vibrations or multimedia for guidance and training.

In another embodiment, a method of training which utilizes a network of wearable sensors to guide and train individual or teams is provided. Wearable sports network is configured to activate the networked wearable sensors to define a player's motion. In addition, the wearable sports network is configured to correct a player's motor skills and make adjustments to optimize a player's or teams' performance.

In yet another embodiment, a method of training which utilizes artificial intelligence to determine precise movements for a player is provided. The artificial intelligence can be customized to correct or adjust a player's motion through the wearables.

In yet another embodiment, a method of training which utilizes robotics to film, monitor or track a player through the wearables that the player put on is also provided.

As developed by applicants, in certain embodiments the invention is provided as a customizable tool kit or platform for building a wearable sports system to provide information, analysis or alerts for an animal, animals, human or humans, comprising a kit or platform of customizable components to meet the needs of a developer, consumer or user of the system. The components include at least one sensor inserted or attached to the animal, animals, human or humans, at least one receptacle configured to contain or receive the sensor, and at least one network unit configured to receive information, analysis or alerts front or transmit information, analysis or alerts to the at least one sensor and analyze, transmit, or both, the information, analysis or alerts obtained or received. The components for selecting the sensor receptacles, the sensors, and the network units are made available to the developer, consumer or user to construct or have constructed a wearable sports system configured to obtain or transmit information, analysis or alerts customized to meet the specific needs of the developer, consumer or user.

In an embodiment of the system, the tool kit or platform of the wearable sports system comes in a variable grouping of preselected sets of kit or platform components or modules of components for constructing the wearable sports system using the kit or platform, and may come together with instructions for building the desired' system. And yet further, in certain embodiments, at least one smart auxiliary component is present in the tool kit or platform.

The tool kit or platform as outlined above, e.g., can be designed for a sports function, health analytics, diagnostic analytics, performance analytics; integration of body sensors, health-devices nano-particles, sports and performance sensors on inanimate objects and sports equipment; sports gear, clothing, stadium, ballpark, park; gym, gymnasium, arena, dome, bowl, circus, coliseum, colosseum; customizable developers' tool kit for biosensors, sensors, performance, medical analytics, oral and systemic diagnosis; integrated, pre-integrated and post-integrated, platforms; any type of medium, secure bidirectional media, multiple media, video, audio, 3D, printing, reporting, analytics, reporting, metadata diagnosis, with geometric tracking, communication networks, analytics, alerting, kinematics for individuals, team sports, organizational groups, animals and humans, communications, software management, data management, instant and long term animal and human analyses, multimedia inputs, visualizations, geometric motion, tracking, kinematics, alerting, therapeutic, electronic medical records, historical analysis, time stamped data, reporting and feedback, positioning, the integrated video can be synced with all wearables and other biosensors in order to produce computer-generated precise movement and greater precision and analytics.

The tool kit or platform in another embodiment includes but not limited to a software control system configured to authenticate, analyze and gather data to guide, enhance performance.

The tool kit or platform in another embodiment includes but not limited to a software control system configured to provide one or more of the functions of tagging, tracking, logging data regarding smart sports equipment, smart sensor wearables as it relates to sports movement.

The tool kit or platform in yet another embodiment includes but, not limited to a software control system configured to provide one or more of the functions of facilitating secure communication, adjusting motor skills, permeating smart particles, and materials, entering secure data points and data sets which assist in coaching, training and athletic performance.

FIG. 1. In these embodiments of the described wearable sports system, an example of a fully integrated performance measurement representing all types of biosensors which could be standardized or customized and provided as a customizable tool kit for humans, and for animals and integrated through one or more, e.g., accelerometers, gyroscope, is depicted. In 110c, 2D or 3D accelerometer models, which dynamically distinguish both 107 an Individual Data filter, and 108, Group Data filters, of 2D and 3D models, multiple visual sensors, for example, videotaping a sports match to distinguish geometric and mathematical relationships between players, the smart basketball or other ball, smart hoop, smart baseball, smart bat, smart gloves, etc., 104 smart wearable devices worn by athletes and animals on any part of the body (head, upper-back, lower hack, legs, knees, shoulder, elbow, hip, ankle, armpit, hand, glasses, contact lens, foot, toe etc). 114 show real-time or near-time reporting and tracking and also provide comprehensive database and historical data analysis and bi-directional communications for authorized coaches and managers as exemplified in 117. Customized guidance adjustment for teams and individual players is presented in 118. In 103, advanced computer, processing is indicated which can evaluate one or more variables originating from an individual (or animal). 102 oral biosensor and 101 biosensor data such as TA, TS, O2, etc., 105 wearables worn on the body, 106 input from all media and other sources (temperature, accelerometer, gyroscope, inertia-sensor, tracking, sensors, camera, video, microphone, speakers, video, speakers, IR, thermal, sensors, positioning, laser, gyroscope, etc.), 113 input from all media, classifications (audio, visual, touch, olfactory, taste, etc.), and 110a dynamic accelerometer data 109 athletes position tracking (XY), indoor positioning (XYZ) and all other data sources. The integration and amalgamation of the aforementioned can comprehensively 109 integrate one player's data on a team or 108 multiple players' data on one or more teams in order to integrate the above with 109 positioning, movement and 111 kinematic relationships from multiple modes. The resulting SGT processed data can utilize probabilistic data association and analytic deterministic data which could help lessen kinematic interference from multiple angles and positions as exemplified in 112. The SGT will provide coaches and managers, for example, integrated tools and greater accuracy as to both a player's physical health and energy, but as it relates to precise movements (110b). Since, in sports, 3D situations can be kinematically ambiguous, or at least very difficult from a tracking algorithm standpoint to be accurately established due to, for example, body parts being close together (e.g., an arm may be pressed against, and blend into another player's back, etc.) when videotaping a sports match or training session. The SGT device collectively provides the coach, trainer or manager 117 secure bi-directional communications, comparatives, historical analysis, time stamped data, reporting and feedback. In addition, the integrated video can be synced with all wearables and other biosensors in order to produce computer-generated precise movement and greater precision and analytics as shown in 116 and 119. Individual "wearable" data can be used as part of a team composite calculated from, a plurality of wearable "inter" and "intra" devices. Thus, External Structures (ES), Smart Sports Equipment (SSE) and Smart Inter-devices (SIRD), for purposes herein, are devices which can be implanted in the oral cavity, for example, Smart External Wearable Devices (SEWD) are defined herein as devices which can be inter-operationally worn on the body or near the body. External Structures (ES) can be defined by any structure, such as, but not limited to, a playing field, stadium, racetrack, court, including any indoor or outdoor environment, which facilitates an athletic or organizational team. Smart Sports Equipment ("SSE") is defined as any equipment needed to facilitate their respective sport and the sport's athlete; such as smart-balls, smart-hoops and smart-base-boards and any other device which facilitates their respective sport. Such sports equipment, e.g., smart-balls, can be tracked, their movements traced, mapped and integrated by means known to those skilled in this art. High-definition videos can be constructed or reconstructed when a network of athletes is equipped with smart-wearables, thus helping solve movement ambiguities when integrated and synced with biosensors, wearables, and video. Thus, to increase positive training (e.g., using vibrational, visional or auditory guidance through wearables and other smart accessories for individuals or, collectively, team guidance, and thereby make performance adjustments determined and set by a coach or staff) skills and greatly enhance performance. Players and coaches can use a variety of smart formats and cellular and wireless platforms to communicate with ear pieces and by other means.

Figure 2:
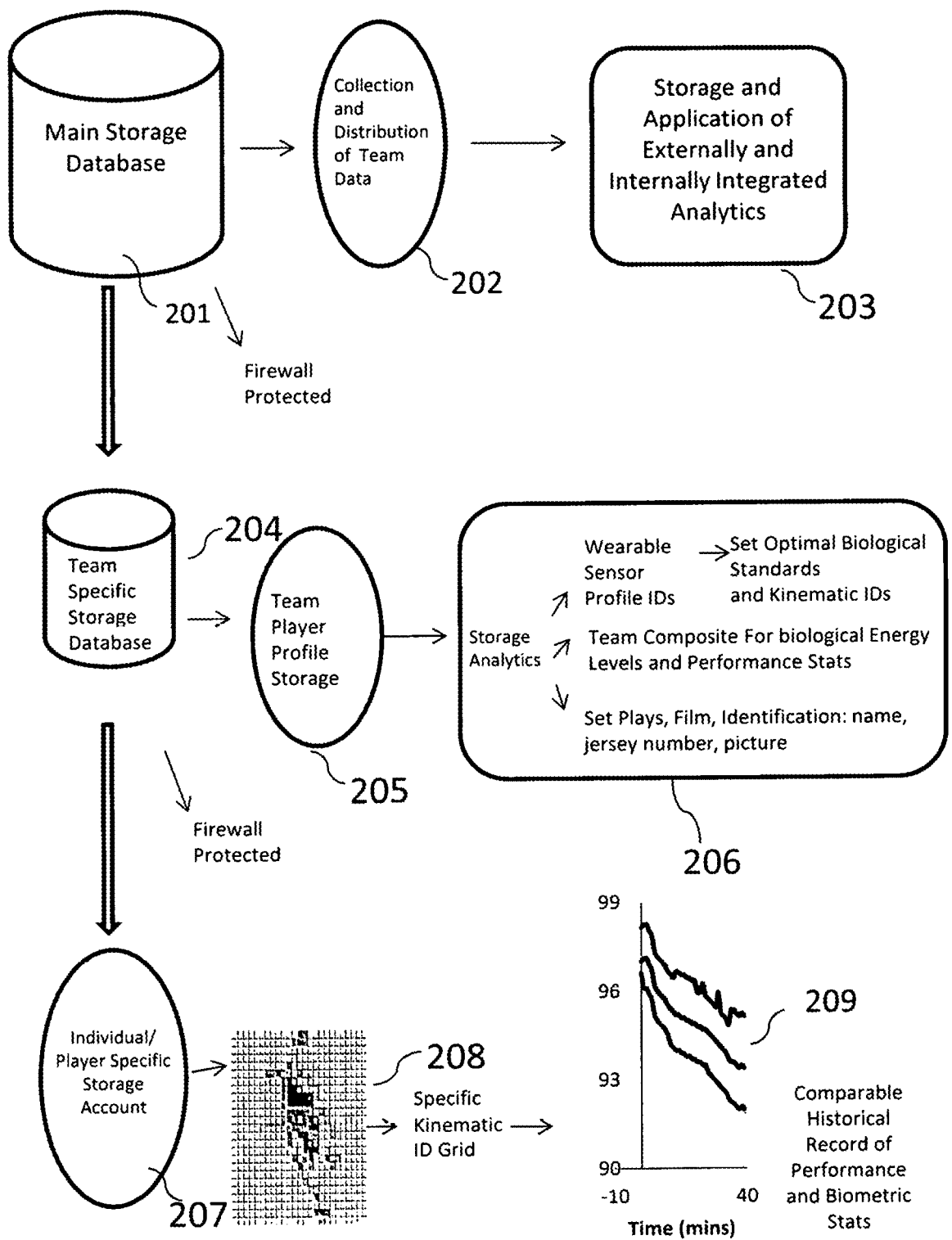
FIG. 2 depicts embodiments which exemplify configuration of database, in accordance with embodiments of the present invention.

FIG. 2. In these embodiments of the described wearable sports system, an example of the tree-shape configuration of storage database is provided. The main storage database 201 is the trunk. Its functions include collection and distribution of team data 202 as well as storage and application of externally and internally integrated analytics 203. Each specific team is the branch derived from the trunk and has its own firewall protected storage database 204. Team player profile storage 205 is viewable by the whole team which consists of set plays, film archives and identification of players by name, jersey number and picture etc. Team player profile storage is the place for storage and application of externally and internally integrated analytics. Information such as wearable sensor profile IDs, optimal biological standards and kinematic IDs etc. 206 are stored here. Team composite for biological energy levels and performance statistics 206, etc. can also be found. Individual/player specific storage account 207 is the leave hanging on the branch which contains player specific analytics such as specific kinematic ID grid 208, comparable historical record of performance and biometric statistics 209, etc.

Figure 3:
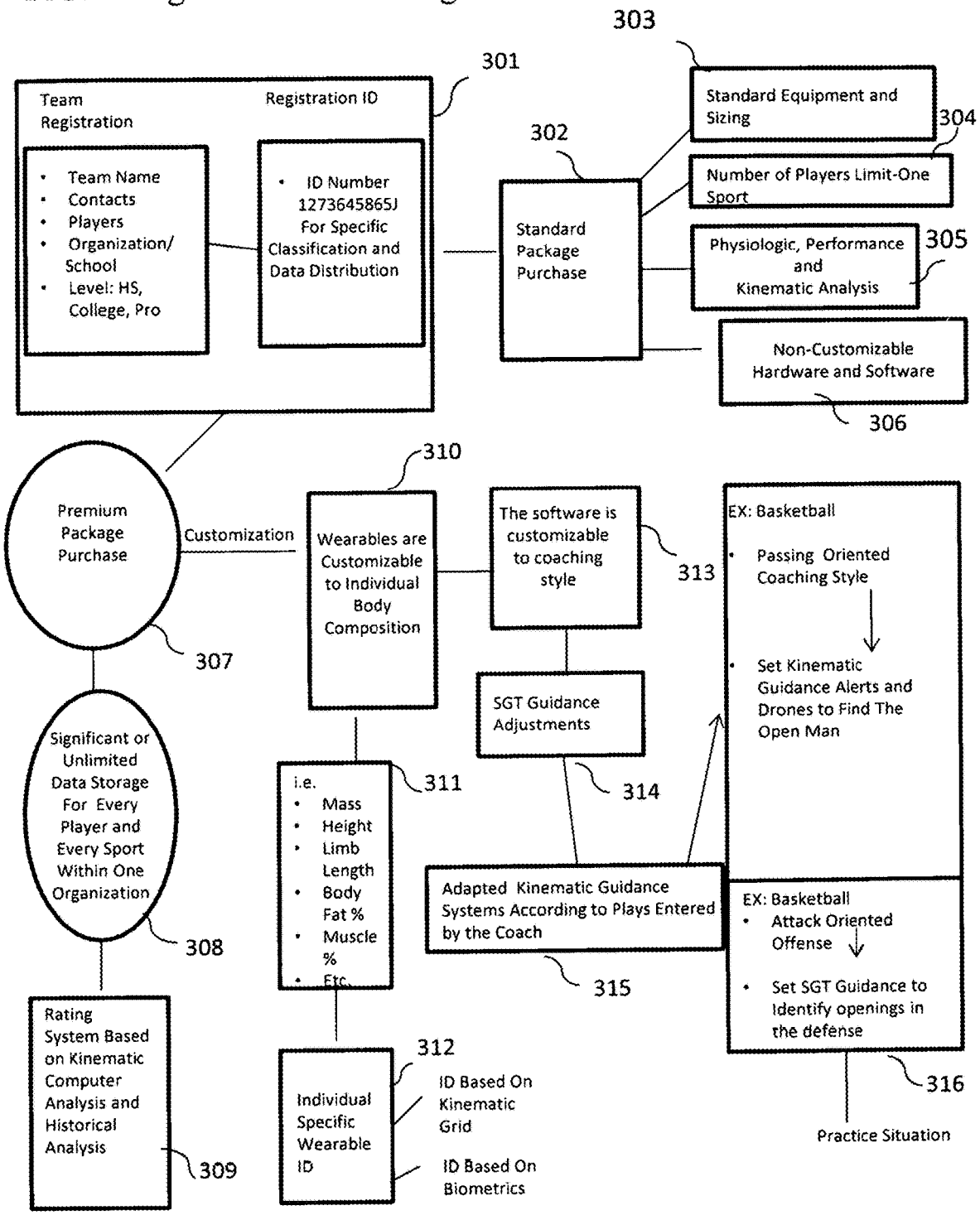
FIG. 3 depicts embodiments which exemplify registration and packages from the wearable sports system, in accordance with embodiments of the pre sent invention.

FIG. 3. In these embodiments of the described wearable sports system, registration and various packages are exemplified. When a team registers, it will be given a registration ID for specific classification and data distribution 301. Registration information consists of team name, contacts, players, organization/school and professional level etc. Standard package 302 is limited to one sport only and has a fixed number of players 304. The package provides standard equipment and sizing 303, non-customizable hardware and software 306, physiologic, performance and kinematic analysis 305, etc. Premium package offers significant or unlimited storage for every player and ever) sport within one organization 308. It also generates a composite rating system based on kinematic computer analysis and historical analysis 309, etc. Both hardware 310 and software 313 are customized. For example, wearables are customizable to individual body composition, i.e. mass, height, limb length, body fat % and muscle % etc. 311 Individual specific wearable ID 312 is given based on kinematic grid and/or physiologics. The software 313 is customizable to coaching style. SGT adjustments 314 are adapted kinematic guidance systems according to plays entered by the coach 315. For example, during basketball practice, a passing oriented coaching style can set kinematic guidance alerts and drones to find the open man while an attack oriented offense can set SGT guidance to identify openings in the defense 316.

Figure 4:
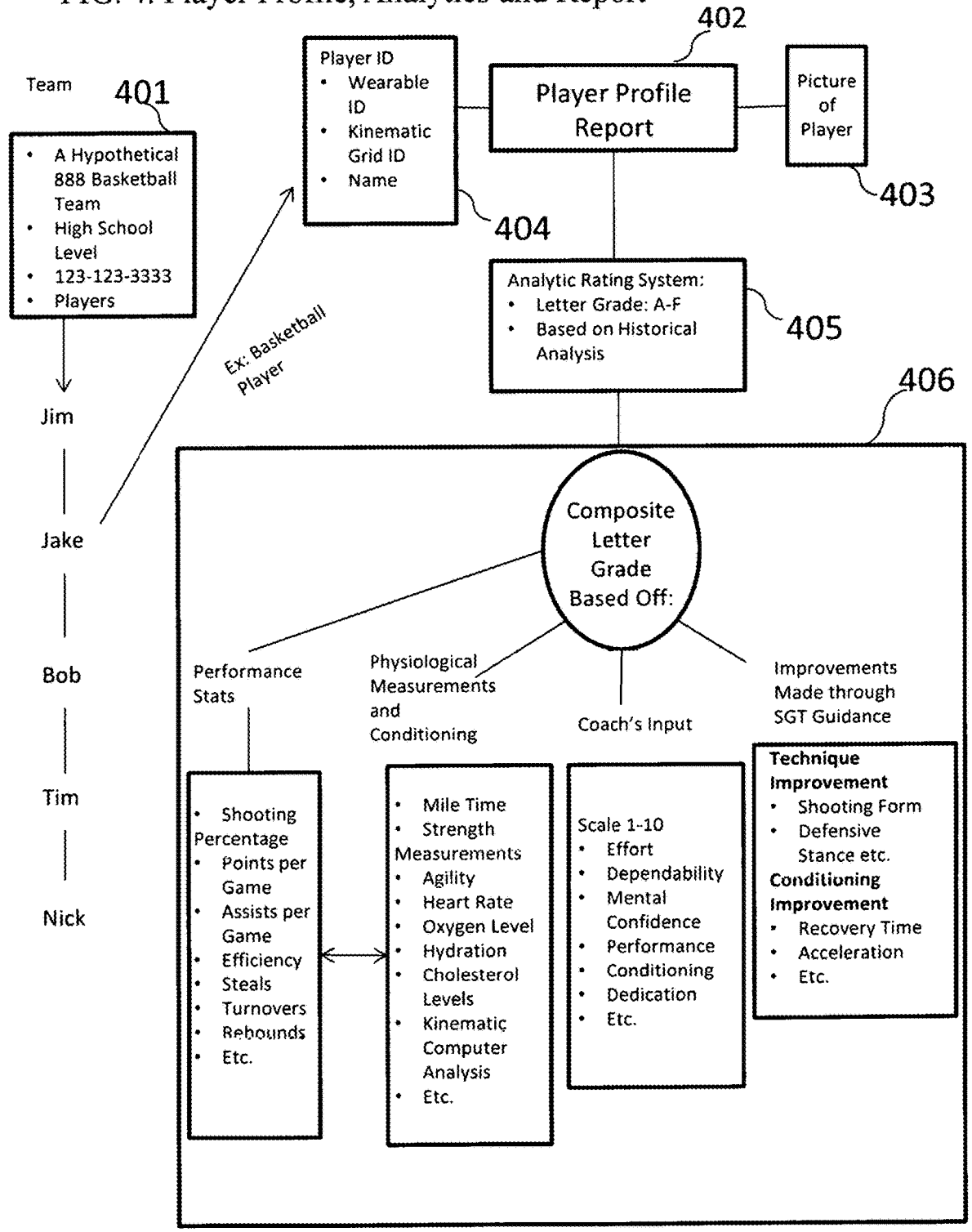
FIG. 4 depicts embodiments which exemplify player profile, analytics and report structure from wearable sports system, in accordance with embodiments of the present invention.

FIG. 4. In these embodiments of the described wearable sports system, an example of analytics and reporting system for an individual player is presented. A basketball team, exemplified in 401 plays at high school level and is composed of player Jim, Jake, Bob, Tim and Nick. Player profile report 402 consists of picture of the player 403, player ID 404 including wearable ID, kinematic grid ID and name as well as SGT analytic rating system 405, etc. Letter grade rating (A-F) 406 is based on historical analysis of performance statistics, physiological measurements and conditioning, coach's input, improvements made through SGT, etc. Performance statistics includes, but not limited to shooting percentage, points per game, assists, per game, efficiency, steals, turnovers, rebounds etc. Physiological measurements and conditioning includes, but not limited to mile time, strength measurements, agility, heart rate, oxygen level, hydration level, cholesterol level, kinematic computer analysis, etc. Coach's input includes, but not limited to effort, dependability, mental confidence, performance, conditioning, dedication, etc. Improvements made through SGT include, but not limited to technique improvement and conditioning improvement, etc.

Figure 5:
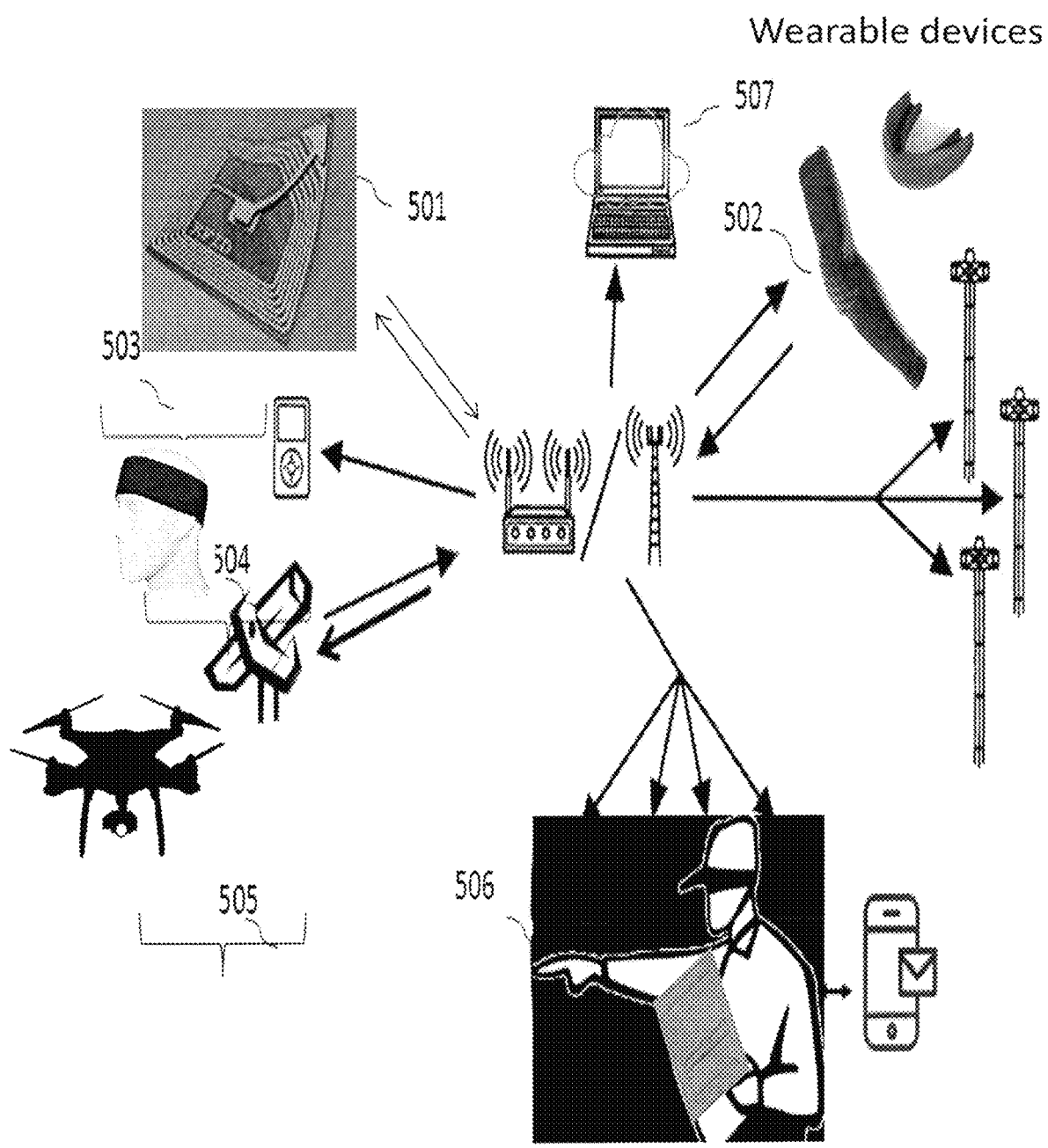
FIG. 5 depicts embodiments which exemplify a wearable sports communication network, in accordance with embodiments of the present invention.

FIG. 5. In these embodiments of the described wearable sports system, an example of wearable sports communication network is depicted. 501 includes addition, monitoring, and management software implemented in order to track a multitude of Radio Frequency Identification (RFID), near field communication, micro- and nano-communication devices, micro- and nano-electronics, etc. data inputs. Active and/or passive, and/or a combination of RFIDs use electromagnetic signals to uniquely distinguish and identify a mobile "TAG" device or stationary "TAG" device. The active RFID identification system tag has its own power source, enabling the unit to broadcast an identifying signal. This extends the range of the tags and capability of communicating advanced data, such as location and other pertinent information, and broadcasts an identifying signal. Passive RFID tags are not powered and rely on active signals from location transmitters for their response. RSSI (Received Signal Strength Indication) is an algorithm that determines the location of an active tag by measuring the power of the radio signals. TDOA (Time Difference of Arrival) is an algorithm that determines the location of active tags by measuring the power of radio signals in real-time. Some RSSI systems have choke-point capabilities that provide an instantaneous notice that a tag has passed a certain point. 502 are examples of various wearable devices which communicate with one or more wireless devices 503, networks, drones 504-505, and subsystems (WiFi, satellites, cellular, etc.) which interface and communicate with the coach or player 506.

Figure 6:
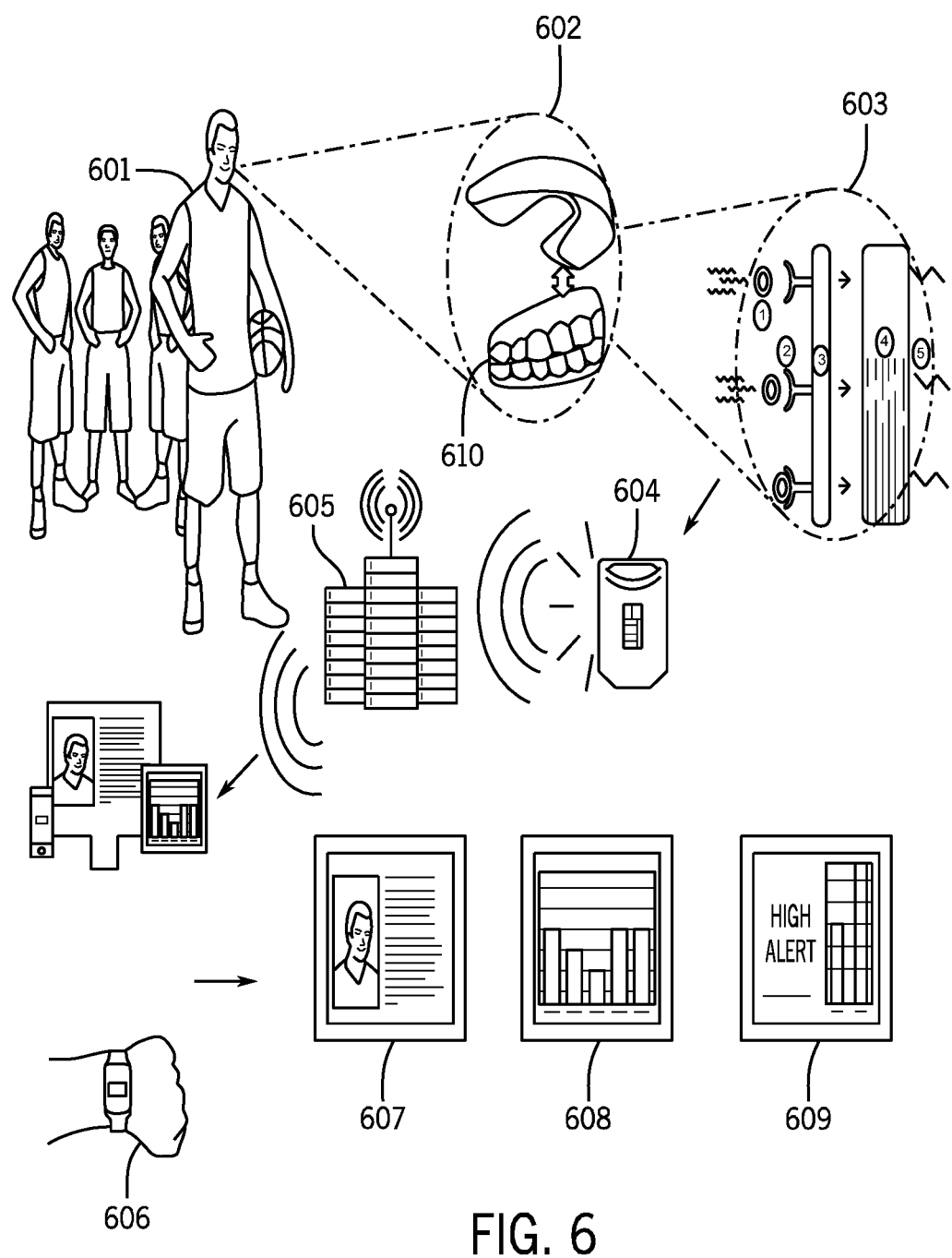
FIG. 6 depicts embodiments which exemplify utilities of a wearable sports system for one or more sports, athletics or organizational participants, or one or more sports teams or organizational groups, in accordance with embodiments of the present invention.

FIG. 6. In these embodiments of the described wearable sports system, any athlete, here exemplified by basketball players 601, can have sensors attached to their teeth, e.g., through an orally inserted device, or any dental device such as a retainer, partial guard, etc. or a combination of an orally inserted device and an accessory device such as a mouth guard, which could be coupled, fitted, attached, etc. to a partial guard or partial retainer 610 etc. The sensor 603 can detect any biologic, biologically relevant molecule, temperature, blood pressure, pulse rate, blood oxygen level, respiration rate, accelerometer, gyroscope, etc. In some situations, biosensors for heart rate, blood oxygen levels, etc. could be placed on the helmet or other head/face gear because these values from the central cardiovascular system might be required, and these could be measured from the carotid artery or its immediate branches. Biosensors or cameras could be placed on helmet parts or other head/face gear near or on the nose to get more accurate respiration rates. SGT devices could collect blood from bleeding due to gum disease, oral trauma and injury, testing, teeth and, gum cleansing such as flossing, water pick, blushing, anything that causing or induce bleeding, pin-prick, etc. SGT device could be inserted in the oral cavity to be bathing in the blood to measure blood glucose levels, blood composition, blood chemicals, medication, etc. As needed, the information or signal can then be transduced, amplified, and processed 603, 602-604. The resulting signal can be transmitted through a RFID tag 603, 605, to an RFID reader, on an accessory, helmet, jewelry, wristband, clothing, smart phone, or others on, in or around the player, exemplified here by a smart wrist band 604. The wearable sports system can also include a RFID tag reader placed within or in proximity to any part of an oral cavity. The signal can then be bi-directionally transmitted to the coach 605. Not shown in the figures, but discussed herein, the smart wristband can also transmit signals from sensors on other locations on the player, other inanimate objects such as a smart ball, hoop, etc. around the player and also with other players on the team. The information transmitted through the smart wrist band to the secure server can be through WiFi, Bluetooth, GPS, NFC, or other wireless methods, and in the absence of immediate conductivity, the information can be temporarily stored in the smart device as explained elsewhere herein 604. The secure server can bi-directionally transmit alerts to pre-selected devices, such as smart phones, iPad, computers, etc. and to personnel such as the player, coach, physician, or others chosen by the player, coach, etc. 606. The alerts can be transmitted when there are deviations from preset range values placed in the system for a biosensor and can also be of varying degrees and tiers as aforementioned. Also, as mentioned elsewhere herein, the physiological data can be viewed for an individual or collectively as a team and can be viewed in different formats such as, e.g., graphs, histograms, or pie-charts. Various screens can show or verbally narrate, e.g., via a talking computer, various information such as different comparatives with other players of a different or the same team, with comparisons made based, on different sizes, ages, weights, gender, etc. or with a player or team's own previous history 607-609.

FIG. 7. In these embodiments of the described wearable sports system, a variety of smart sport guards are exemplified. Unfixed dental devices 701 are defined as ones not permanently attached to the jaw bone, but as possibly attached to the gum or teeth. Temporary biosensor mouth guards 702 and 703 have a generally shortened life span compared to fixed devices, but they may be placed in the oral cavity for from several minutes to several months (but typically are not designed for placement, e.g., for several years). Biosensors are optionally attached to or embedded in these devices. These biosensors could be custom-made by 3D printing. Biosensor physiological measurements 704 include, but not limited to, oxygen saturation, blood pressure, blood glucose level, blood sugar, heart rate, lactic acid build up, body temperature, hydration, amount of strain on muscles and tendons and bones, cholesterol levels, eyesight and recovery time etc.

FIG. 8 represents an embodiment of the integration of Sports Guidance Technologies. As illustrated in FIG. 1, coaches and players can use a variety of integrated biosensors, kinematic, alert and media technology to analyze all the factors that play into performance, thus improving performance 801. Environmental factors such as humidity and altitude etc. can have impacts on performance 802. The SGT device, not only senses how these environmental conditions can alter performance levels and physiological characteristics within players, but it also provides adaptations or adjustments in a player's techniques or preparation in order to minimize the negative effect that some environmental factors may have on a player's execution during a competition. Biosensors are also integrated into the SGT device 803. Once certain physiological attributes such as temperature, heart rate, or blood pressure etc. is identified within a player, coaches and trainers can then set optimal set points for players 804. For example, in order for a player to perform at his or her best, their physiological attributes such as temperature can't be too loss or too high. So, their SGT device will detect if a player's physiological attributes go beyond or below a certain point according, to the set points that coaches and trainers have prescribed, and then immediately alert the coach or trainer through a mobile device. This can effectively reduce the possibility of injuries and damage to body functions. The SGT sensors also analyze the performance statistics of a player along with their physiological data 805. As a result, the SGT device can identify how the physiological conditions of a player can directly impact the performance of a player during a competition, and can also provide different ways for players to increase their health, which ultimately leads to better performance. During training, SGT device can also integrate an aspect of kinematic analysis to improve not only performance, but also team chemistry. GPRS drone locators can be placed in the practice vicinity 806, and can film, monitor, and also track each player on the field through the wearables that the player puts on 807. In addition, the drones can be set to identify a player of where another certain player on the field/court is, through the player identification of the wearables that players have on 808. When a drone needs to alert a player of where another player is on the court, vibration units within the wearables of players will vibrate. The location and strength of the vibration will alert the player of another set player's position on the field so that a play can be made through these 2 players; thereby, improving the chemistry between the 2 players 809. During individual based skills training, the wearable sensors of the SGT device can also identify the position and movement of the player while he or she goes through certain exercises by means of kinematic identification and computer pixilation. After the precise movements of the player are tracked, the SGT sensors, drones and computers can compare the movements of the player to the precise movements and techniques of a professional sports player 810. If a certain movement proves to be inaccurate, then the wearables can send directionalized vibrations to the player and also suggest corrections to a player's movement, positon, and technique 811 and 812. This correction method can be known as the Record Correction Method (RCM). Another possibility for personal training with the SGT device is to superimpose the movements of a player and virtualized players and their movements for a more interactive and effective training scenario 813. Every single factor from environmental, physiological and kinematic etc., can be analyzed by the SGT sensors as it correlates to performance, so that players and coaches can better understand the relationship between these factors and performance 814; thereby, having a better understanding of not only maximizing performance, but also keeping performance at a peak level for the longest period of time possible for each player. The player's motion, position during competitions, and execution will all be improved, while training techniques and conditioning can also be refined 815. This is meant to be a flexible tool for coaches to use as a part of their training program in order to maximize the effectiveness of training as well as performance 816.

FIG. 9. In these embodiments of the described wearable sports system, an example of external integration through environmental factors is provided. Environmental factors 901 including altitude, noise level, humidity, temperature and wind speed, etc., can have direct impact, on physiological attributes including oxygen saturation, heart rate, temperature, blood glucose, blood pressure and hydration etc., which results in performance adjustments 903 as detailed in 904. For examples, when the environmental sensors detect high altitude and the biosensors detect lowered oxygen levels affecting muscle activity, the SGT device may give instructions of conservative play and using more muscles etc. When the noise level is detected high by the environmental sensors and psychological stimulation is shown by the biosensors, the SGT device may recommend breathing techniques to relax and calm down the body. As an increased rate of fatigue is determined by the biosensors at high temperatures, the feedback can be the increase in substitution rate. Wind speed reduces the accuracy in football throws, therefore the SGT device can suggest throwing adjustment based on kinematic analysis. Low temperature leading to lowered muscle activity, thereby the SGT device may instruct more emphasis on warm ups. Wet ground resulted from the rain increases the chance of improper footing during football game. Subsequently the SGT device may recommend staggered steps and focuses on passing. Low humidity lowers hydration level, as a result, the SGT device may suggest drinking more water, and so on.

FIG. 10. In these embodiments of the described wearable sports system, an example of internal integrations through physiological measurement in relation to performance is provided. Physiological measurements 1001 including oxygen saturation, blood pressure, calories, temperature and hydration etc. along with overall biostatistics physicality 1002 can have direct impact 1003 on performance statistics 1004 including shot percentage, efficiency, turnover ratio, points per game, speed and agility etc. Sport injuries including fatigue, exhaustion and heatstroke, etc. could be resulted from some unidentified physiological conditions such as lowered hydration levels, lowered oxygen levels and abnormally high temperatures, etc. 1005. Biosensors can be applied to alert hydration levels, oxygen level and body temperature, etc. As a result, performance adaptation can be planned which includes drinking more water before games, substitutions, stretch before games and warming up, etc. Biosensors which provide real-time alerts on the health conditions can effectively prevent injury and help coach make better decisions 1006.

FIG. 11. In these embodiments of the described wearable sports system, an example of sensor set points, data collection, alert and report is presented. Sensor predetermined set points for physiological parameters such as temperature, oxygen saturation level, heart rate and blood sugar etc. are listed in 1101. Biosensors monitor oxygen saturation level of each player on the team throughout a period of physical activity is shown in 1102. An alert 1102 is transmitted when the oxygen saturation level from player John drops to 90% which is a sensor set point for intermediate low alert as listed in 1101.

FIG. 12. In these embodiments of the described wearable sports system, graphical representation of data collection, alert and report is exemplified. The profiles of oxygen saturation level for each individual player (John, Bart, Tim, Jake and Tom) during a basketball game are presented in 1201. Oxygen saturation level of 90% is set as an alert limit. Intense physical activity in the game causes decrease in oxygen levels for all the players although the extent of reduction varies. Seventeen minutes into the game, John's oxygen saturation level drops to the alert limit 90%, so the coach replaces him with a substitute. As a result, John's oxygen level starts to recover 1201 & 1202. For a different player Bart, only seven minutes into the game, the coach notices that his rate of oxygen decrease is much faster compared to other players in the team, indicating suboptimal physical conditions. So the coach immediately replaces Bart even before his oxygen level hits the alert limit 1201. Subsequently, Bart's oxygen level recovers. And when the coach sees Bart's oxygen level reach and maintain at a high level for some time, he puts Bart back to the game in 17 minutes as a substitute for John. Similar scenario happens to Tim who is replaced by Jim in 12 minutes but he does not return to the game due to his slow recovery. Jake and Tom play the whole game since their rates of oxygen decrease are slow and both performances are strong. Jim doesn't play at the beginning, so his oxygen level is kept constant until he substitutes Tim in 12 minutes. According to the sensor set points, "safe high" and "safe low" levels for oxygen saturation are plotted along with "alert limit" as shown in 1202 & 1203. Overall team energy and physiological composite are plotted in 1203. Compared to the big fluctuations of oxygen level in each individual player, the change in the overall team composite is relatively small and the average maintains above the "safe low" level. Even at the beginning of the game, the reduction in oxygen level for the team is much slower. By substituting players at 3 critical moments (7 minute, 12 minute and 17 minute), the team average oxygen level manages to maintain a competitive level throughout the game. An inflection point occurs when a player's oxygen, level stops decreasing and starts to recover after he is replaced by a substitute as shown in 1201. Thus the inflection point can be used to track substitution of the players during the game.

FIG. 13 elaborates on the kinematic factors to maximize performance through the kinematic, identification, analysis, and directional guidance of each player as a part of the external integration of SGT sensors and software. Drones are applied to film and monitor the field as well as track the players by the alerts that players have on their SGT wearables 1301. Vibrations in different locations of the wearables are utilized to alert players where another certain player is on the floor 1302. By doing so, it increases the chance to score for a certain team and ultimately improves team chemistry. For example, in basketball game, the sensors vibrate in the left arm sleeve of a player. As a result, the player knows that there is another player on his left that he can pass to and possibly get a shot off. By using vibration oriented communications, team chemistry among players can be improved. The kinematic information of each player that is tracked can be sent by a high definition video in real time or near real time to the coaches 1304. Coaches are also able to set certain sensors and vibrations to certain players. For examples, in basketball, coaches can specifically set vibration alerts between the point guard and a center so that the point guard can be alerted of where the center is. As a result, the point guard may then have the information he needs to get the center the ball for him to get a wide open layup 1305. SGT can superimpose the movements of a player onto the virtualized players and their movements for a more interactive and effective training scenario 1306. For example, training with a virtualized player replication that has superimposed movements can be used to correctly guide the player during training so that a comprehensive learning environment can be created between a virtualized player and the players who is training. As a result, players will learn what exactly to do in certain game situations 1306. Precise movements of the player can be tracked. And then the SGT sensors, drones and computers will compare the movement of the player to the precise movements and techniques of a professional sports player. If a certain movement proves to be inaccurate, then the wearables can send directionalized vibrations to the player and also suggest corrections to a player's movement, position and technique. This correction method can be known as Record Correction Method (RCM) 1307. For example, if the defensive stance of a basketball player is off balance, the Record Correction Method not only alerts the player that his form is off, but can also guide him to have the defensive form of a professional basketball player through directionalized vibration that can be paired with coaching as well.

FIG. 14 exemplifies the information explained FIG. 13. The scenario is in the context of a basketball game where there are 5 offensive players on the field. Drones are used to monitor the court and track players through wearables that the players put on 1401. In this instance, sensors and vibrations on each player's wearables illustrate how the sensors can not only direct players into making the right plays that ends in scoring for the team, but also improves team chemistry as well. The location of the vibration on the wearables is what determines the general location where the player is as well as the general angle of which the pass of the basketball should be directed towards. The strength of the vibration determines the distance as well as the velocity in which a player has to throw the basketball in order for the ball to get to the next player most effectively. Low vibrations represents the distance of one player to another player is long while a stronger vibration means the distance between 2 players is shorter 1402. In this specific example, the player gets the rebound from one side of the basketball court and looks down the floor 1403. The drones also detect the player who got the rebound. Immediately after, drones detect another open player farther down the court that is sprinting down the floor. Once the open player is identified as the smartest and most effective play, a low vibration in the frontal location of the player with the ball's headband alerts the player that he needs to throw the ball at a 90-degree angle east 1404 with a high velocity in order to get it to the next most effective open man 1405. The open man 1405 on the other end of the floor will also get a vibration that alerts him that a pass is coming his way. Once he receives the pass, another vibration on the left side of his headband alerts the player that there is another open man 1406 right by the basketball hoop that can score easier than he will. The strong consecutive vibration 1405 tells the player that he is close to the open man 1406, which means he needs to throw a pass that is at 135-degrees southeast which is a quick zip pass in order to most effectively transfer the ball to the open man 1406 by the basket. Finally, the open man 1406 receives a medium vibration that alerts him that a ball is coming his way for him to score. This set play identified by the wearable sensors ultimately results in a play for the team to score and improves their on-court knowledge of basketball plays as well as their team chemistry with one another.

FIG. 15. In these embodiments of the described wearable sports system, an example of a fully integrated diagnostic and performance measurement system is provided. 1505 represents a secure host server which can be implemented and utilized by one or more individuals, one or more animals, or one or more organizations. In addition, the present invention can include a privatized internal server host and subsystems as well as one or more external hosted alert servers. A plurality of collective data can be derived from several SGT oral measurements including, but not limited to, the integration of any type of wearable as described in FIG. 1 and other embodiments in the present invention. A plurality of biosensor data can inform all smart devices 1502, all wearable devices whether smart or not smart, all RFID readers, all can be examined and analyzed in order to determine the degree of an alert (low, medium or high) being dispatched, through various templates 1507 referred to today as cloud networks which includes all forms of smart devices, one or more pagers, SMS, Faxes, emails, GIS mappers, beacons (XYZ) telephones, PSTN devices 1508 (Voicemail, IVR, ASR, TTS), satellite phones and other forms of communication. The alert can be dispatched to any computer-aided device or emergency dispatch if the SGT device detects higher than average or abnormal metabolic ranges, for example. The SGT device can use one or more templates to help delineate these physiological ranges as exemplified by 1501. 1506 exemplifies the packaging of biosensor parameters as defined (Definition 1, Definition 2, Definition 3 . . . ) by the individual, coach, team and organization etc. In addition, the alerts can be streamed, packeted or stored on the server or on, the person(s) or animal(s). Alerts can be represented through preset criteria notification icons converted to SMS, SMS or icons converted to voice alerts, visual notification, touch (vibration) auditory notification and customized through one or more algorithms and diagnostics and secure databases, servers and networks can be used. In addition, bi-directional or multi-directional 1504 API/TCP data, i.e., SSL (128-Bit) data transmissions can use SSL and a message relay using cellular data services 1503 transmitted through one or more host servers. Data application can be the triggering of the alert as previously described, and can be automated (M2M), manual or a combination of both. SGT alerts can also be combined with APP public general alerts for one or more geographies.

FIG. 16. In these embodiments of the described, wearable sports system, an equine, exemplified here by a race horse 1601, has biosensors attached to a mouth-bit, bit-guard, bit-gag, lip-strap, or other dental device 1602. The biosensor 1603 can detect any biologic, biologically relevant molecule, temperature, blood pressure, pulse rate, blood oxygen level, respiration rate, gyroscope, accelerometer, etc. SGT devices could collect blood from bleeding due to gum disease, oral trauma and injury, testing, teeth and gum cleansing such as flossing, water pick, blushing, anything that causing or induce bleeding, pin-prick, etc. SGT devices could be inserted in the oral cavity to be bathing in the blood to measure blood glucose levels, blood composition, blood chemical, medication, etc. As needed, the information or signal can then be transduced, amplified, and processed 1603, 1602-1604. The resulting signal can be transmitted through a RFID tag 1603, 1605, to an RFID reader on, e.g., an accessory or other item attached to the horse, including a collar, rein, saddle, or on a horse-rider or jockey, jockey's smart phone, or others, on, in, or around the horse, which could read the biosensors located in the bit when in the horse's mouth, exemplified here by a smart rein 1604. In some situations, biosensors for heart rate, blood oxygen, gyroscope, accelerometer, inertia-sensor, tracking sensors, camera, video, microphone, speakers, etc. could be placed on the horse equipment such as, but not limited to, headstall, headgear, ear-poms, blinker hood, hackamores, noseband, cheese-band, bridle, blinders, winkers, ornaments such as phalerae and sallongs, etc. Various values which integrate the oral bit guard data from the central cardiovascular system could assist in measuring both performance and health through the SGT devices. Biosensors or cameras could be placed on a blinker hood, nose-piece, or attached to the horse's nose or other facial parts to get more accurate respiration rates. In addition, a heart-monitoring device, heart-rate, or respiration monitoring device can be attached to the saddle or other horse equipment, attached to or associated with the horse. Horse heart rate can be monitored by placing biosensors on a manure catcher, or a diaper such that the sensors are under the tail at the tailbone. The heart rate can also be measured by wireless biosensors on horse's leg or other body pail. To measure performance, accelerometers, gyroscope, inertia-sensors, etc. can be placed at various parts of a horse's body, such as its legs, neck, torso, etc. The SGT device can thus include an RFID tag reader placed within or in proximity to any part of an oral cavity, temporarily or permanently. Not shown in the figure, but disclosed elsewhere herein, similar to an application for an athlete, the smart horse-rein, e.g., can also communicate a signal from sensors on the horse and other inanimate objects around the horse and from other horses. The signal can then be bi-directionally transmitted to a secure server 1605. The information transmitted through the smart horse-rein, e.g., to the secure server can be through WiFi, Bluetooth, GPS, NFC, MiWi, Lura, microwave, radio signals radio transmission and receiving, computer network or other wireless methods, and in the absence of immediate conductivity, the information can be temporarily stored in the smart device as explained elsewhere herein 1605. The secure server can bi-directionally transmit alerts to pre-selected devices, such as smart phones, iPad, computers, etc. and personnel such as the owner, veterinarian, jockey, or others chosen by the owner 1606. The alerts can be transmitted when there are deviations from preset range values placed in the system for a biosensor and can also be of varying degrees and tiers as aforementioned. Also, as mentioned elsewhere herein, the physiological data can be viewed in different formats such as, e.g., graphs, histograms, or pie-charts. Various screens can show or verbally narrate, e.g., via a talking computer, different information such as different comparatives with other race horses of different, similar or the same sizes, ages, weights, gender, etc. or with the horse's own previous history 1607-1609.

FIG. 17 presents examples of wearable network integrated for performance measurement. Smart earbud 1701 is made using crowd noise reduction technology to decrease noise level from environment which allows oral communications among coaches and players to be heard more clearly. Biosensors including temperature, heart rate, blood O2, accelerometers, gyroscope and others can all be embedded in the smart earbud 1701, smart arm band 1703, smart head band 1704, smart mouth guard or retainers 1702 etc. All the wearable sensors placed in all parts of the body can be integrated by the wearable sports system for performance measurements. Biometric measurement sensors such as, e.g., a temperature sensor, pulse, O2 levels ran be integrated with performance sensors to measure inertia, speed, gait, movement etc. In other words, the present invention as previous described can network any worn body wearable to measure an animals or persons walking, running, balance, stress levels, gait etc. It is understood by anyone familiar with the art that even a seemingly minor change in balance, between one leg or four, one arm to another can lead to further injury. Micro changes in gait, motion, balance and other performances can be detected earlier through the present invention. One or more accelerometers and/or gyroscopes may be integrated into the mouth guard or body of a horse, animal or human to provide information regarding movement of the wearer. For instance, accelerometers and/or gyroscopes can provide information regarding; shock movement, gait, slant, tilt, limp etc. In addition, environmental conditions such as temperature, humidity, altitude, wind and other conditions could be factored with speed, inertia, distance, time and biometrics. It is understood by anyone familiar with the art that a plurality of these conditions could be used for any animal or human sport, any and all weather conditions and any and all biometric measurement, inertia measurement, movement measurement etc. In another embodiment of the present invention, for illustration purposes shows an example of the race horse or show horse industry. Since race horses and show horses exert a great amount of stress on the limbs, various gyroscopes and sensors could be coupled in order to measure each limb's movement, impact and gait differentials. This data could be collected to help provide training adjustments for example, forecast future problems and methods of prevention.

FIG. 18 depicts embodiments which exemplify a wired equine smartbit hardware device in accordance with the present invention. A bridle is a piece of equipment used to direct a horse. As defined in the Oxford English Dictionary, the "bridle" includes both the headstall that holds a bit that goes in the mouth of a horse, and the reins that are attached to the bit. The bridle can be attached to a smartbit which instead of directly communicating wirelessly, it is wired to the bridle on the left side or right side of the smartbit. It is obvious to anyone familiar with the art that the bridle is the headgear used to control a horse, consisting of buckled straps to which a bit and reins are attached to horse tack. In addition, A bit is a type of horse tack used in equestrian activities, usually made of metal or a synthetic material, and is placed in the mouth of a horse or other equid and assists a rider in communicating with the animal. 1805 represents the bars of the mouth in an interdental region where there are no teeth. The present invention as described includes various biosensors embedded or attached to a horsebit and held on a horse's head by means of a bridle and has reins attached for use by a rider. 1804 represents an electronic wire connection leading from the bit to outside of the oral cavity. The electric wire connection connects the smartbit's biosensors and microprocessors with an outside battery 1801 and wireless communication devices. 1801 represents a battery connected to the smartbit from outside of the horse's oral cavity. It is understood by anyone familiar with the art that one or more batteries could be wired to the smartbit device or module. 1808 represents one or more biosensors embedded or attached to the smartbit and wired to various horse tack equipment 1807 as represented previously described in the present invention. In addition, FIG. 18b presents depicts embodiments which exemplify a wired equine smartbit hardware device in accordance with the present invention. 1805b and 1801 represent components, such as a microprocessor 1807b, GPS, accelerometers, battery, wireless communication and a plurality of biosensors, etc. The smartbit device as exemplified by 1802b makes contact with the surface of the equines tongue as biologically shown in 1803b These wireless communication devices could be Wifi, Bluetooth, Miwi, Lora, etc. In addition, it is understood by anyone familiar with the art that any physiological measurement for any animal and human can be measured through the present invention e.g., pH levels, possible to measure blood components such as but not, limited to water for hydration or dehydration, glucose etc. via sensors on horse gear and cat and dog collar, or human wearable no matter where located on the anatomy or networked and communicated. 1804b exemplifies the bottom of the electronic smartbit design where the sensors are placed. In addition, the smartbit can be encased to prevent moisture entering the device. In addition, the device could be encased by metal 1801b or a hard plastic which could help prevent damage by the horse or user. 1806b represents a portion of the smartbit which could contain, components which communicate, power, sense, measure and feeds information to the server and a mobile device (tablet, reader, cell phone, laptop, smart watch, PC etc.). It is understood that any wireless protocol could be utilized depending on the type of sport and application. It is also understood that wireless communication is the transfer of information or power between two or more points are not connected by an electrical conductor (wire) from the smartbit to outside of the mouth as described by FIG. 18a as contrasted by 18b which contains an inter mouth battery and oral communication device for example. In addition, it is understood by anyone familiar with the art that the most common wireless technologies use radio. Radio waves distances can be short, such as a few meters for television or as far as thousands or even millions of kilometers for deep-space radio communications. It encompasses various types of fixed, mobile, and portable applications, including two-way radios, cellular telephones, and wireless networking. In addition, the Other examples of applications of radio wireless technology include GPS units which could be used to long distance horse racing which extends beyond the geography horse racing track. In addition, the present invention includes drones which are equipped with data sensors, timers, distance measurements, locators, cameras and environmental monitors etc. The airborne drone application described in the present invention can be utilized for not only the equine industry but the sports industry in general.

FIG. 19 presents embodiments which exemplify include the wireless hardware and software integration and communication between animals and humans. 1901 equine smartbit hardware device in accordance with the present invention. 1905 represents various mobile devices used to retrieve information. It is obvious to anyone familiar with the art that mobile devices could include any wearable device as represented by 1904. In addition, 1902 exemplifies a jockey's helmet which can interface the equines biosensor information as previously detailed in the present invention as exemplified by 1901, track racing locators, GPS, time measurements, distance measurements, jockey helmet ear communicators, jockey bi-directional microphones for audible information, etc. 1903 exemplifies a near-time or real-time database and network. The it is obvious, by anyone familiar with the art that one or more horses, animals, humans in one or more geographies could communicate and add or retrieve information.

FIG. 20 presents a secure and customized database through the developer's toolkit. This information can be customized to include all real-time or near-time data; including but not limited to the animal's or person's historical biosensor data, data analytics, performance analytics (performance time, distance, environmental, location etc.). In addition, the customized database can be serialized, personalized and coupled with various registration datasets.

FIG. 21 presents 2101 multivariate/multidimensional alerting technologies which compare the analytics of one or more components of performance as previously described, one or More components of biometric data, one or more components, analytics, mean averages, standard deviation of various levels of performance which can range anywhere from low or below average to higher than average etc. it is understood by anyone familiar with the art that any analytics variable, set-points can be a component factor or an influencing factor with any degree of alerting. In addition, it is obvious to anyone familiar with the art that alerting variance and differentials can be established from standardized set-points, i.e., age of the horse, etc., or customized by the user through the developer's toolkit. In addition, it kits obvious to anyone familiar with the art that any secure mobile device can register the ownership, environmental conditions, the riding jockey, the expected performance times and distances, the environmental factors such as wind, outside temperature, humidity, altitude, etc. and other pertinent racing conditions.

FIG. 22 presents various methods when determining gait, speed distance, start time, stop time, 2203 time splits, 2205 racetrack field physical location, 2201/2202 biosensor hardware locators 2202 on the physical horse, in the oral cavity or touching the animal, on the software, network, etc. 2204 represent mobile access to one or more performance components, one or metre environmental components, one or more biometric measurements. In addition, a horse start-time, stop time, interval distance splits of any distance and time factor can be measure manually (electronic stop watch), stationary modules and nodes, accelerometers, cellular global positioning, worn on the horse or placed around the racetrack and show geography. It obvious that any and all distance and time performance measurement protocols or a combination of one or more performance technology could be used in any combination de pending on time and distance accuracy. It is obvious to anyone familiar with the art that recreational horse owners fear example will not require as much performance and biometric accuracy as the professional sports industry.

FIG. 23 presents sensors airborne drone observance 2306 which can video, time, measure the racetrack as it relates to the horse race, practice race and time interval. In addition, the present invention can include software for the equine as represented by 2302 and drone 2306 application to measure one or more environmental conditions, gait, track splits of any distance on any racetrack show field represented by 2303. 2307 shows any fixed node which measure speed, distance and stationary node placement around the track or geography. It is obvious to anyone familiar with the art that the placement of these stationary measurements could rely time splits, time intervals and distance demarcation as represented by 2303. 2304 exemplifies the previously described mobile interface which receives the data and information communicated from the drone, horse, jockey, trainer or person. 2301 represents the measurement and distance, time variation of the distance of the inner track (close distance a horse can run from the inside track with other distances measurement or differential/variable away from the inside lane. The distance from the inside lane from outer lanes greatly increases the distance of the race. 2305 refers to the separation of measurements and distance as it relates to one or more stationary nodes. It is obvious to anyone that understands the art that the 2306 drone could be equipped with one or more sensors, high definition cameras, environmental sensors, motion sensors, timers, distance measuring devices, GPS and GPRS devices and be unlimited to mobility, speed and tracking capabilities.

FIG. 24 presents and exemplifies an example of human 2407 and 2402/2403 animal physiological interaction and sensor measurements and information data 2413, comparative sensor data, biometric data, tracking data, environmental informational data (humidity, altitude, temperature, wind, barometric, and footing (paw, hoof) conditions, distance traveled informational data, caloric data, historical data, alerting information, location information, graphic information, analytic information, deviation comparatives, communication information, timestamp information, feedback information, access information, data usage information, drone based information and other information, 2406 presents an example of physiological sensor measurements for an animal, in this case a dog, where a dashboard display could compare the heart rate, pulse, Spo2, and any other biometric measurements worn or attached to a pet and information transmitted with its human owner or trainer and received through one or more mobile devices presented by 2408 or accessories presented by 2409, 2410. An embodiment of the present invention can include a database 2413 as previously described which software applications can include asynchronously or synchronously log timestamped biometric comparatives between the pet and its owner 2412. In addition, other embodiments of the present invention include animals such as a horse 2404 and a rider's 2411 timestamped biometrics and other sensor information and metrics such as optimal O2 levels, optimal heartrate, optimal temperature, etc. when performing. In addition, other embodiments can include comparative biometric and sensor measurements analytics between pets, and humans 2405 and between a human 2401 and horse 2412. In addition, the data comparatives and information between humans and their animal counterparts can be securely communicated through the API and customized for not Only recreational purposes but for medical, professional and even social benefits.

Also, for purposes of this description, the terms "couple," "coupling," "coupled,' "connect," "connecting," or "connected" refer to any manner known in the art or later developed in which energy is allowed to be transferred between two or more elements, and the interposition of one or more additional elements is contemplated, although not required. Conversely, the terms "'directly coupled," "directly connected," etc., imply the absence of such additional elements. Signals and corresponding nodes or ports may be referred to by the same name and are interchangeable for purposes here.

It should be understood that the steps of any exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments of the present invention.

As used herein in reference to an element and a standard, when used, the term "compatible" means that the element communicates with other elements in a manner wholly or partially specified by the standard, and would be recognized by other elements as sufficiently capable of communicating with the other elements in the manner specified by the standard. The compatible element does not need to operate internally in a manner specified by the standard.

It will be further understood that various changes in the details, materials, and arrangements of the parts which have been described and illustrated in order to explain the nature of this invention may be made by those skilled in the art without departing from the scope of the invention as expressed in the claims.

I claim:

1. A system comprising:
   a first device configured to be inserted or attached to a first wearable comprising first equipment to interact with an animal or a human;
   a second device configured to be inserted or attached to a second wearable comprising second equipment to interact with another animal or another human;
   each of the first and second wearables further comprising a smart sensor receptacle for a sensor and microprocessor device, each of the first device and second device further comprising one or more sensors contained within or upon each of the first and second wearables, the one or more sensors operable to measure biometrics of the animal or human equipped with the first and second devices; and
   at least one interface communicatively coupled with the first and second devices with a network, the at least one interface configured to:
      receive information from the first and second devices, the information including the biometrics of the animal or human equipped with the first and second devices,
      simultaneously utilize the information from the first and second devices,
      compare the biometrics of the animal or human of the first device and the biometrics of the another animal or human of the second device,
      inform the animal or human of the first device or the another animal or another human of the second device on adjustments to optimize combined activity of the animal or human of the first device and the another animal or another human of the second device.

2. The system of claim 1 wherein one or more functions generated by one or more sensors inserted or attached to the human and animal of the first or second device is selected from a mobile device communication computer-generated precise movement and greater precision or analytics.

3. The system or claim 1 wherein the system further comprises a database compilation of the animal's exercise times and performance comparative entries between a human and animal.

4. The system of claim 1 wherein the system further comprises a database compilation of one or more physiological attributes for humans and animals prior to starting the exercise.

5. The system of claim 1 wherein the system further comprises a database compilation of one or more physiological attribute for humans and animals throughout the exercise interval.

6. The system of claim 1 wherein the system further comprises a database compilation of one or more physiological attribute after each exercise and resting interval for humans and animals.

7. The system of claim 1 wherein the system further comprises a database compilation of one or more physical attribute after the exercise is ended.

8. The system of claim 1 configured to synchronously analyze and communicate animal and human performance as it relates to various body workings and sensors.

9. The system of claim 1 configured to asynchronously analyze and communicate animal and human performance as it relates to various body workings and sensors.

10. The system of claim 1 wherein the system utilizes airborne droves to wirelessly communicate and relay information from sensors worn asynchronously by the animal and human.

11. The system of claim 10 wherein the system utilizes airborne drones to communicate video information to the database.

12. The system of claim 10 wherein the system utilizes airborne drones to measure distance and route.

13. The system of claim 10 wherein the system utilizes airborne drones to measure time and speed.

14. The system of claim 1 configured to provide an alerting signal to a human's smart device by voice as it relates to one or more physiological measurements derived from the animal and human sensors.

15. The system of claim 14 wherein the system is further configured to operate a communication device in order to communicate the animal's biometrics alerts to the human through various vibration patterns.

16. The system of claim 1 wherein the system further comprises wireless accessory devices which interconnect with an animal's information through audio communication.

17. The system of claim 1 wherein the system further comprises a historical database of the animal's physiological measurements from which comparisons are to be made to human physiological measurements.

18. The system of claim 17 wherein the system integrates to mobile platforms in order to transfer and receive animal biometric and physiological data measured by worn sensors.

19. The system of claim 17 wherein the system compares timestamp analytical data communicated between animals to human on mobile devices in real-time and near-time.

20. The system of claim 17 wherein the system further comprises of software configured to provide the distance traveled by humans and animals.

* * * * *